US011023856B2

United States Patent
Laster et al.

(10) Patent No.: US 11,023,856 B2
(45) Date of Patent: Jun. 1, 2021

(54) PROVIDING IMPLANTS FOR SURGICAL PROCEDURES

(71) Applicant: Smith & Nephew, Inc., Memphis, TN (US)

(72) Inventors: Scott Kennedy Laster, Memphis, TN (US); Stuart Raymond Morris-Hipkins, Humarock, MA (US); David Clark Kelman, Somerville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 28 days.

(21) Appl. No.: 16/174,832

(22) Filed: Oct. 30, 2018

(65) Prior Publication Data

US 2019/0073632 A1 Mar. 7, 2019

Related U.S. Application Data

(63) Continuation of application No. 15/101,701, filed as application No. PCT/US2015/043306 on Jul. 31, 2015.
(Continued)

(51) Int. Cl.
*G06Q 10/08* (2012.01)
*G16H 50/30* (2018.01)
(Continued)

(52) U.S. Cl.
CPC ....... *G06Q 10/0875* (2013.01); *G06Q 10/087* (2013.01); *G16H 10/60* (2018.01);
(Continued)

(58) Field of Classification Search
CPC .. G06Q 10/0875; G06Q 10/087; G06Q 50/22; G16H 40/20; G16H 50/30;
(Continued)

(56) References Cited

U.S. PATENT DOCUMENTS 5,574,828 A 11/1996 Hayward et al.
7,433,827 B2 10/2008 Rosenfeld et al.
(Continued)

FOREIGN PATENT DOCUMENTS

EP 2060986 A1 5/2009
EP 2063373 A1 5/2009
(Continued)

OTHER PUBLICATIONS

Just in time (Business), Wikipedia, reprinted from http://en.wikipedia.org/wiki/Just_in_time(business) on Jul. 28, 2014.
(Continued)

*Primary Examiner* — Linh Giang Le
(74) *Attorney, Agent, or Firm* — Troutman Pepper Hamilton Sanders LLP

(57) ABSTRACT

Methods, systems, and apparatus, including computer programs encoded on a computer storage medium, for providing implants for surgical procedures. In some implementations, a model that has been trained using data indicating characteristics of other patients and items used in surgeries for the other patients is obtained. Using the model and patient characteristics for a patient, such as the height and weight of the patient, the items needed for a surgery for a particular patient can be identified. For example, the likelihoods that different sizes of an implant component will be needed can be identified and used to determine which sizes of components should be provided at a medical facility and in the operating room for the patient's surgery.

12 Claims, 14 Drawing Sheets

Related U.S. Application Data

(60) Provisional application No. 62/032,303, filed on Aug. 1, 2014.

(51) Int. Cl.
    *G16H 50/50*     (2018.01)
    *G16H 10/60*     (2018.01)
    *G16H 40/20*     (2018.01)
    *G16Z 99/00*     (2019.01)
    *G16H 20/40*     (2018.01)

(52) U.S. Cl.
    CPC ............ *G16H 20/40* (2018.01); *G16H 40/20* (2018.01); *G16H 50/30* (2018.01); *G16H 50/50* (2018.01); *G16Z 99/00* (2019.02)

(58) Field of Classification Search
    CPC ........ G16H 50/50; G16H 10/60; G16Z 99/00; G06F 19/00
    See application file for complete search history.

(56) References Cited

U.S. PATENT DOCUMENTS

| | | |
|---|---|---|
| 7,630,947 B2 | 12/2009 | Pandya et al. |
| 7,937,660 B2 | 5/2011 | Binkert |
| 8,069,055 B2 | 11/2011 | Keen |
| 8,615,473 B2 | 12/2013 | Spiegel et al. |
| 8,635,082 B2 | 1/2014 | Woods et al. |
| 2005/0251418 A1 | 11/2005 | Fox, Jr. et al. |
| 2007/0272747 A1 | 11/2007 | Woods et al. |
| 2008/0201174 A1 | 8/2008 | Ramasubramanian et al. |
| 2009/0089034 A1 | 4/2009 | Penney et al. |
| 2010/0274591 A1 | 10/2010 | Wells |
| 2012/0209394 A1 | 8/2012 | Bojarski et al. |
| 2013/0269714 A1 | 10/2013 | Roe et al. |
| 2014/0013565 A1* | 1/2014 | MacDonald ............ G06F 19/32 29/407.05 |
| 2014/0081659 A1* | 3/2014 | Nawana ................... G01L 5/00 705/3 |
| 2015/0032467 A1* | 1/2015 | Rapp .................... G06Q 10/067 705/2 |

FOREIGN PATENT DOCUMENTS

| | | |
|---|---|---|
| WO | 2007009263 A1 | 1/2007 |
| WO | 2010068212 A1 | 6/2010 |
| WO | 2010074781 A2 | 7/2010 |
| WO | 2010124282 A1 | 10/2010 |
| WO | 2011156597 A1 | 12/2011 |
| WO | 2011156601 A2 | 12/2011 |
| WO | 2013032642 A1 | 3/2013 |
| WO | 2013036496 A1 | 3/2013 |
| WO | 2014043661 A2 | 3/2014 |

OTHER PUBLICATIONS

Hospital Uses Data Analytics and Predictive Modeling to Identify and Allocate Scarce Resources to High-Risk Patients, Leading to Fewer Readmissions, reprinted from https://innovactions.ahrq.gov/profiles/hospital-uses-data-analytics-and-predictive-modeling-identify-and-allocate-scarce-resources, date: Jun. 4, 2014 (accessed Mar. 9, 2015).

Ast et al., The Reduction and Implant-Related Errors and Waste in Total Knee Arthroplasty Using a Novel, Computer Based, e.Label and Compatibility System, Journal of Arthroplasty (2014), 29:132-136.

International Search Report and Written Opinion for PCT/US2015/043306 dated Oct. 30, 2015.

Chinese First Office Action for CN20158005359.6 dated Jan. 4, 2019 (with English Translation).

Chinese Second Office Action for CN201580053539.6 dated Oct. 25, 2019 (with English translation).

European Office Action for EP15828309.3 dated Nov. 12, 2019.

European Supplementary Search Report and Written Opinion for EP 15823809.3 dated Mar. 5, 2018.

Australian Examination Report No. 1 for Australian Patent Application No. 2015296014 dated Apr. 28, 2020.

* cited by examiner

| Implant Size | Minimum Safety Stock | Predicted Need | Current Inventory | Difference |
|---|---|---|---|---|
| 9 | 1 | 2 | 2 | -- |
| 10 | 1 | 3 | 4 | +1 |
| 11 | 2 | 6 | 7 | +1 |
| 12 | 2 | 7 | 6 | -1 |
| 13 | 3 | 10 | 8 | -2 |
| 14 | 2 | 6 | 7 | +1 |
| 15 | 2 | 6 | 8 | +2 |
| 16 | 2 | 6 | 3 | -3 |
| 17 | 1 | 3 | 1 | -2 |
| 18 | 1 | 2 | 2 | -- |

PROVIDING IMPLANTS FOR SURGICAL PROCEDURES

CROSS-REFERENCE TO RELATED APPLICATION

This application is a continuation application of U.S. patent application Ser. No. 15/101,701, filed on Jun. 3, 2016, and titled "Providing Implants for Surgical Procedures," which is a U.S. national stage filing under 35 U.S.C. § 371 of International Application No. PCT/US2015/043306, filed Jul. 31, 2015, which claims the benefit of U.S. Provisional Application No. 62/032,303, filed Aug. 1, 2014, the entire contents of each of which are hereby incorporated by reference.

FIELD

This disclosure relates to providing implants for surgical procedures.

BACKGROUND

Various items may be used during medical procedures, such as implants, instruments, medicines, bandages, and so on. In many instances, it is difficult to determine which sizes of implant components will be needed, since the decision of which size to use is often determined after surgery begins.

When needed items are not readily available in the operating room, risks to the patient increase significantly. Delays in obtaining needed implants may increase the length of the procedure, potentially increasing the amount of anesthesia the patient needs and increasing opportunities for infection. If the correct implant is not available, a surgeon may attempt to use a size that is not ideal, which may cause pain or reduced function later on, and potentially the need for a future revision surgery. In some instances, if the surgeon's preferred implant system is not available, the surgeon may attempt to use a different implant system that the surgeon is not as familiar with, which may increase risks of surgeon error.

There are also significant risks to patients due to potential human error in selecting implant components. Implanting the wrong size of implant component, or implanting incompatible components together, can increase the risk of poor patient outcomes, such as pain, reduced function, premature failure requiring revision procedures. Prior to surgery, it is often difficult for surgeons to determine which sizes and types of implants will be needed for a given patient. Techniques that rely on radiographic templating are subject to inaccuracies and human error, and require patients to be exposed to X-rays. Further, manual templating requires additional surgeon time, and results may not be communicated to the medical facility where the surgery is to be performed.

Providing implants for surgery may also be challenging because the size or type of implant needed may not be determined until the time of surgery or shortly before. For example, surgeons sometimes need to make intraoperative decisions that affect which implant is used. After making bone cuts on a femur during a knee replacement procedure, for example, the resulting bone shape may be in between implant sizes. Some surgeons prefer to use the larger size, and some surgeons prefer to use the smaller size. If a surgeon's preferences are not known, many different implants may need to be provided so that the appropriate implant is available.

As a result, determining which implants, tools, and other items to provide at a medical facility, and in what quantities, can be challenging for surgical teams as well as for hospital administrators.

SUMMARY

Various techniques may be used to assist medical facilities to provide appropriate implants for surgical procedures. In some implementations, surgical management systems may predict the inventory needs of a medical facility, including likelihoods that different sizes and types of items will be needed. With accurate predictions of upcoming needs, the medical facility may obtain needed items in an efficient manner, limiting risks to patients and reducing excessive storage requirements and other overhead. In some instances, the predicted information about upcoming needs allows a medical facility to obtain the quantities implants and other items needed with a defined level of confidence, e.g., 90%, 95%, or 98%, while not obtaining excess quantities, e.g., without unneeded quantities above a predetermined amount. The medical facility's limited storage and other resources can be customized to include the items predicted to fill the needs of an upcoming set of patients, rather than being occupied by items selected without information about the patients.

In some instances, items may be ordered on an on-demand or just-in-time basis as a result of the predictive modeling, rather than facilities inefficiently carrying inventory that is unlikely to be used. Based on the predictions, the inventory of a medical facility may be adjusted in a variety of ways, including ordering components from a manufacturer or other supplier, expediting a shipment in transit, or requesting items from other medical facilities. Further, automated surgical management systems may reduce the amount of human effort required to make implants and other items available to medical staff at the time of surgery, reducing costs and the likelihood of errors.

In some implementations, a surgical management system may use patient characteristics, such as sex, age, height, and weight, to predict the sizes of implants that are likely to be needed at a medical facility. Automated prediction techniques can overcome or avoid many of the challenges of manual size prediction. For example, for some procedures, physicians manually attempt to estimate which size of implant to use by taking an x-ray and placing a template over the x-ray image. There are frequently errors in the estimated size, for example, due to incorrect magnification of the x-ray image. These manual estimates are often only about 80% accurate even relative to a range of plus or minus one size from the predicted size. In addition, determining a size with a template can be time consuming, and many physicians do not make an estimate. Even if a physician estimates an implant size, the estimate is usually not provided to the operating room or to hospital staff in advance of the surgery, and thus is not available for the medical facility to set inventory levels.

However, as discussed herein, implant sizes and needs for other items may be predicted based on basic patient information that is available in the medical records of the medical facility. These predictions can permit a medical facility to streamline inventory levels while limiting the risk that a needed item will be unavailable at the time of surgery. A medical facility may set appropriate inventory levels that match the likely needs for scheduled procedures and/or the demographics of the population served by the medical facility, ultimately reducing the cost of services provided to patients. The predictions may be used to determine inventory levels that are as low as is possible without exceeding a defined level of risk of the inventory not meeting the needs of the medical facility.

The cost of providing health care may also be reduced by using data analysis to identify the factors that contribute to successful outcomes for patients. For example, data about various medical procedures can be analyzed to determine which surgical techniques or other actions most commonly result in favorable outcomes. The identified actions can be considered for use to improve outcomes for other patients, for example, as best practices that may be implemented by multiple surgeons or medical facilities. Similarly, analysis of data about medical procedures performed by a particular surgeon or medical facility may be analyzed to determine the specific causes that the surgeon or medical facility is receiving results that are favorable or unfavorable. Patient compliance with pre-operative and post-operative regimens can be tracked and correlated with patient outcomes as part of the analysis. Patient characteristics, such as sex, age, weight, height, and comorbidities, may also be tracked and assessed relative to patient outcomes. In addition, historical data for medical procedures may be analyzed to predict which future patients may be at risk for unfavorable outcomes, as well as what steps would be likely to increase the likelihood of a more favorable outcome. By proactively identifying at-risk patients and addressing their needs—in some instances, even before surgery has occurred—the costs resulting from potential complications and unfavorable outcomes may be avoided.

In addition, health care can be enhanced by enhancing communication between medical facilities and suppliers of medical products. In some instances, a surgical management system may allow real-time or near real-time feedback between medical facilities and suppliers. For example, a product selected for use in a medical procedure can be scanned and identified. In response to the scan, a signal may be sent to the surgical management system, which may automatically cause the inventory for the item to be replenished. For example, the surgical management system may determine which contracts or prices are applicable, and submit an order to a supplier to purchase the used item at the contracted price. The process of adjusting inventory at the medical facility, including identifying the need to re-order items and effecting transactions, can be automatic and seamless. Automated inventory adjustment may allow for greater accuracy than manual ordering. In addition, the efficiency of the surgical management system may allow hospitals and other medical facilities to manage inventory of at least some items using a just-in-time delivery model and to avoid the costs of maintaining a large inventory.

In one general aspect, a method of determining quantities of implant components of different sizes is performed by one or more computers. The method includes accessing data indicating (i) multiple scheduled orthopaedic surgeries that are scheduled to be performed at a particular medical facility during a particular period of time, and (ii) physical patient characteristics for patients corresponding to the scheduled orthopaedic surgeries, the physical patient characteristics including at least a height of each of the patients and a weight of each of the patients. The method includes performing a set of actions for each particular scheduled orthopaedic surgery of the scheduled orthopaedic surgeries. The set of actions includes identifying an implant component that is used during surgeries having a surgery type corresponding to the particular scheduled orthopaedic surgery. The set of actions includes identifying, from among a set of multiple models corresponding to different implant components, one or more models corresponding to the identified implant component, the one or more models having been generated using relationships between items used in past surgeries for other patients and physical characteristics including heights and weights of the other patients, the one or more models indicating correlations between (i) physical patient characteristics including at least height and weight and (ii) multiple different sizes of the implant component. The set of actions includes using the identified one or more models to generate, based on the height and the weight of the patient corresponding to the particular scheduled orthopaedic surgery, probability measures for multiple different sizes of the implant component, each of the probability measures indicating a probability that a particular size of implant component will be used in the particular scheduled orthopaedic surgery. The method includes determining, based on an aggregated set of probability measures generated for the scheduled procedures, a quantity of each of multiple different sizes of multiple different implant components to provide at the particular medical facility for the particular period of time.

Implementations of this and other aspects discussed herein include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

Implementations may also include one or more of the following features. For example, determining the quantity of implant components may include: identifying a predetermined confidence level representing a desired level of confidence that implant components needed for the scheduled orthopaedic surgeries will be available at the particular medical facility; and for at least a first implant component of the one or more implant components, determining, based on the aggregated sets of probability measures, quantities of the first implant component to provide at the medical facility in each of the multiple different sizes to achieve the predetermined confidence level.

In some implementations, the method may include accessing records indicating an inventory of implant components at the particular medical facility; comparing (i) the determined quantities of implant components of the multiple different sizes with (ii) recorded quantities of implant components of the in the inventory at the particular medical facility as indicated in the accessed records; determining, based on the comparison, a difference between the determined quantities of implant components and the recorded quantities of implant components; and in response to determining the difference, providing, to the medical facility, a message indicating the difference between the determined quantities of implant components and the recorded quantities of implant components.

In some implementations, the method may include providing, over a computer network and to one or more computers associated with the particular medical facility, data indicating the determined quantities of different sizes of implant components prior to the particular time period.

In some implementations, the scheduled orthopaedic surgeries include joint arthroplasty surgeries for a particular joint, and determining a quantity of each of multiple different sizes of multiple different implant components includes determining a quantity for each of multiple sizes of each of multiple different implant components that, when assembled, form a prosthesis for the particular joint.

In some implementations, using the identified one or more models to generate a probability measure for each particular size of multiple different sizes of the implant component includes: using a first model to generate, based on the height of the particular patient and the weight of the particular patient, first probability measures corresponding to different sizes of a first implant component used in orthopaedic surgeries of the particular orthopaedic surgery type; and using a second model to generate, based on the height of the particular patient, the weight of the particular patient, and the probability measures generated using the first model, second probability measures corresponding to different sizes of a second implant component that is used together with the first implant component in orthopaedic surgeries of the particular orthopaedic surgery type.

In some implementations, using the identified one or more models to generate probability measures for multiple different sizes of the implant component includes: using the identified one or more models to generate a probability measure for each of the multiple different sizes of the implant component based on the height of the particular patient and the weight of the particular patient and further based on a sex of the particular patient, an age of the particular patient, a race of the particular patient, or a body mass index of the particular patient.

In some implementations, the method includes: after the scheduled orthopaedic surgeries are completed, receiving data indicating sizes implant components that were implanted during the scheduled orthopaedic surgeries; based on the data indicating the sizes of the implant components that were implanted, altering parameters of the models in the set of multiple models to change probabilities indicated by the models for one or more sizes of implant components; and using the updated models to generate probability measures for different sizes of implant components for a second set of scheduled orthopaedic surgeries.

In some implementations, the method includes: identifying a particular surgeon that is designated to perform one of the scheduled orthopaedic surgeries; and accessing data indicating preferences of the particular surgeon. For the scheduled orthopaedic surgery that the particular surgeon is scheduled to perform, using the identified one or more models to generate probability measures for multiple different sizes of the implant component may include: generating a first set of probability measures for the multiple different sizes of the implant component; and modifying the first set of probability measures based on the preferences of the particular surgeon to generate a second set of probability measures. Determining the quantity of each of multiple different sizes of multiple different implant components may include determining the quantities based on aggregated probability data generated using the second set of probability measures.

In some implementations, accessing the data indicating the preferences of the particular surgeon includes: accessing data indicating previous surgeries performed by the particular surgeon; selecting, from among the previous surgeries performed by the particular surgeon, orthopaedic surgeries of the particular orthopaedic surgery type; and determining the preferences of the particular surgeon based on correlations between sizes of implant components used in the selected orthopaedic surgeries and the heights and weights of patients in the selected orthopaedic surgeries.

In some implementations, identifying the one or more models corresponding to the implant component and the particular orthopaedic surgery type includes: identifying a particular geographic region associated with the particular medical facility; and identifying one or more models generated to provide probability measures, according to the demographics of the particular geographic region, for different sizes of an implant component.

In some implementations, using the identified one or more models to generate the probability measures includes determining a distribution curve that indicates probabilities of different sizes of the implant component being used in a surgery for the particular patient. Determining the quantity of each of multiple different sizes of multiple different implant components may include: aggregating, using the distribution curves determined for different patients, multiple distribution curves for sizes of a first implant component to generate an composite distribution curve across different sizes of the first implant component; and selecting, for each particular size of the first implant component, a quantity of the particular size of the first implant component according to the value of the composite distribution curve corresponding to the particular size.

In some implementations, determining the quantities of the multiple different sizes of implant components includes determining, based on the aggregated probability measures, different quantities of each of multiple different sizes of a first implant component such that, if the determined quantities of the first implant component are provided at the particular medical facility: a confidence level for the particular medical facility equals or exceeds a predetermined minimum confidence level, the confidence level for the particular medical facility representing a likelihood that the quantities of the different sizes of the first implant component that are needed to perform the scheduled orthopaedic surgeries will be available at the particular medical facility, and the quantities of the first implant component will not exceed a level needed to achieve the minimum confidence level by more than a predetermined maximum excess amount.

In some implementations, the predetermined minimum confidence level represents at least a 90% probability that needed quantities of the first implant component will be available; the confidence level for the particular medical facility is determined based on probability measures generated using one or more of the multiple models; and the predetermined maximum excess amount comprises a safety stock amount in excess of the quantities of the first component needed to achieve the predetermined minimum confidence level.

In another general aspect, a method of selecting sizes of an implant component for a patient can be performed by one or more computers. The method includes accessing, from the one or more data storage devices, (i) data indicating physical characteristics of the particular patient including a height of the particular patient and a weight of the particular patient, (ii) data indicating a particular orthopaedic surgery type for a scheduled orthopaedic surgery for the particular patient, and (iii) one or more models generated using relationships between implant components used in past surgeries for other patients and physical characteristics of the other patients including heights and weights of the other patients. The method includes determining, based on the particular orthopaedic surgery type for the scheduled orthopaedic surgery, that an implant component is used in surgeries of the particular surgery type. The method includes, in response to determining that the implant component is used in surgeries of the particular orthopaedic surgery type, identifying one or more models corresponding to the implant component and the particular orthopaedic surgery type, the identified one or more models indicating correlations between (i) physical patient characteristics including at least height and weight and (ii) multiple different sizes of the implant component. The method includes using the identified one or more models to generate, based on the height and weight of the particular patient, a probability measure for each particular size of multiple different sizes of the implant component, each of the probability measures indicating a probability that an implant component of the particular size will be used in the scheduled orthopaedic surgery of the particular patient. The method includes selecting, from among the multiple different sizes, a subset of the sizes of the implant component to provide during the scheduled orthopaedic surgery based on whether the probability measures corresponding to the respective sizes satisfy one or more thresholds.

Implementations may include one or more of the following features. For example, in some implementations, determining that the implant component is used in surgeries of the particular orthopaedic surgery type comprises identifying, based on the particular orthopaedic surgery type for the scheduled orthopaedic surgery, multiple different implant components are used together in surgeries of the particular orthopaedic surgery type. Identifying one or more models may include identifying multiple models, each of the multiple models being configured to indicate probabilities of use of different sizes of an implant component corresponding to the model. Using the selected one or more models may include using the identified multiple models to generate, based on the height and weight of the particular patient, a set of probability measures for each of the multiple different implant components, each set of probability measures indicating probabilities that different sizes of the corresponding implant component will be used in the scheduled orthopaedic surgery of the particular patient. Selecting a subset of the sizes comprises selecting, for each of the multiple different implant components, a subset of the sizes of the implant component to provide during the scheduled orthopaedic surgery. The method may include providing a subset of the implant component sizes for each of the multiple different implant components that are used together in surgeries of the particular surgery type.

In some implementations, the orthopaedic surgery type for the scheduled orthopaedic surgery type is a joint arthroplasty for a particular joint, and the multiple different implant components that are used together in surgeries of the particular orthopaedic surgery type are components that, when assembled, form a prosthesis for the particular joint.

In some implementations, wherein using the identified one or more models to generate a probability measure for each particular size of multiple different sizes of the implant component includes: using a first model to generate, based on the height of the particular patient and the weight of the particular patient, first probability measures corresponding to different sizes of a first implant component used in orthopaedic surgeries of the particular orthopaedic surgery type; and using a second model to generate, based on the height of the particular patient, the weight of the particular patient, and the probability measures generated using the first model, second probability measures corresponding to different sizes of a second implant component that is used together with the first implant component in orthopaedic surgeries of the particular orthopaedic surgery type.

In some implementations, using the identified one or more models to generate a probability measure for each particular size of multiple different sizes of the implant component includes: using the identified one or more models to generate a probability measure for each of the multiple different sizes of the implant component based on the height of the particular patient and the weight of the particular patient and further based on a sex of the particular patient, an age of the particular patient, a race of the particular patient, or a body mass index of the particular patient.

In some implementations, the method includes providing, to the operating room for the scheduled orthopaedic surgery during the scheduled orthopaedic surgery, data indicating the selected subset of sizes of the implant component.

In some implementations, the method includes providing, in advance of the scheduled orthopaedic surgery, data identifying the selected subset of sizes of the implant component.

In some implementations, the method includes: after the scheduled orthopaedic surgery is completed, receiving data indicating a size of the implant component that was implanted in the particular patient; based on the data indicating the size of the implant component that was implanted in the particular patient, altering parameters of the one or more models to change probabilities indicated by the one or more models for one or more sizes of the implant component; and using the updated one or more models to generate probability measures for different sizes of the implant component for a scheduled surgery of another patient.

In some implementations, the method includes: identifying a particular surgeon that is designated to perform the scheduled orthopaedic surgery for the particular patient; and accessing data indicating preferences of the particular surgeon. Delecting a subset of the sizes of the implant component to provide during the scheduled orthopaedic surgery may include: identifying a subset of sizes of the implant component based on whether the probability measures corresponding to the respective sizes satisfy the one or more thresholds; modifying the subset of sizes based on the preferences of the particular surgeon; and selecting the modified subset of sizes of the implant component to provide during the scheduled orthopaedic surgery.

In some implementations, accessing the data indicating the preferences of the particular surgeon includes: accessing data indicating previous surgeries performed by the particular surgeon; selecting, from among the previous surgeries performed by the particular surgeon, orthopaedic surgeries of the particular orthopaedic surgery type; and determining the preferences of the particular surgeon based on correlations between sizes of implant components used in the selected orthopaedic surgeries and the heights and weights of patients in the selected orthopaedic surgeries.

In some implementations, identifying the one or more models corresponding to the implant component and the particular orthopaedic surgery type comprises: identifying a particular geographic region associated with the particular patient or with a surgeon designated to perform the scheduled orthopaedic surgery; and identifying one or more models generated to provide probability measures, according to the demographics of the particular geographic region, for different sizes of the implant component.

In another general aspect, a method is provided for adjusting an inventory of medical supplies at a medical facility. The method being performed by one or more computers. The method includes receiving data indicating patient characteristics of a particular patient. The method includes inputting the patient characteristics of the particular patient to a predictive model that has been trained to predict items likely to be used in surgeries. The predictive model has been trained using data indicating characteristics of other patients and items used in surgeries for the other patients. The method includes receiving, from the predictive model in response to inputting the patient characteristics of the particular patient, data indicating items likely to be used in a planned surgery for the particular patient. The method includes adjusting an inventory of medical supplies at a medical facility where the planned surgery for the particular patient is to be performed based on the data indicating items likely to be used in the planned surgery for the particular patient.

In another general aspect, a method is provided for adjusting an inventory of medical supplies at a medical facility. The method being performed by one or more computers. The method includes accessing, for each of multiple patients, data indicating a scheduled medical procedure to be performed for the patient at the medical facility and characteristics of the patient. The method includes obtaining, for each of the multiple patients, probability data determined based on the patient's characteristics, the probability data indicating likelihoods that items will be used during the medical procedure for the patient. The method includes aggregating the probability data for the multiple patients to generate predicted inventory data that indicates predicted quantities of the items needed for the medical procedures of the multiple patients. The method includes accessing current inventory data indicating quantities of the items that will be available at the medical facility. The method includes determining differences between the predicted inventory data and the current inventory data. The method includes adjusting the amounts of at least some of the items at the medical facility based on the differences between the predicted inventory data and the current inventory data.

In another general aspect, a method is provided for adjusting a predictive model configured to predict medical supplies needed for a medical procedure based on characteristics of the patient receiving the medical procedure. The method may be performed by one or more computers. The method includes accessing patient data indicating characteristics of a particular patient. The method includes accessing prediction data that indicates outputs that a predictive model provided based on receiving the patient data as input, the prediction data indicating probabilities that particular items would be used in a surgical procedure for the particular patient. The method includes accessing usage data indicating items that were used in the surgical procedure for the particular patient. The method includes adjusting the predictive model based on the prediction data and the usage data.

In another general aspect, a method is provided for tracking and analyzing outcomes of medical procedures. The method may be performed by one or more computers. The method includes storing pre-operative data for multiple patients in one or more databases, the pre-operative data indicating pre-operative regimens for the patients and levels of compliance with the pre-operative regimens by the patients. The method includes storing post-operative data for the multiple patients in the one or more databases, the post-operative data indicating post-operative regimens for the patients and levels of compliance with the post-operative regimens by the patients. The method includes storing outcome data for the multiple patients in the one or more databases, the outcome data indicating outcomes of medical procedures of the multiple patients. The method includes analyzing the data stored in the one or more databases to identify correlations of the pre-operative data and the post-operative data with different outcomes indicated by the outcome data. The method includes determining, based on the correlations, measures indicating how compliance or non-compliance with elements of pre-operative or post-operative regimens contribute to the different outcomes indicated by the outcome data. The method includes providing, on a user interface, the measures indicating how compliance or non-compliance with elements of pre-operative or post-operative regimens contribute to the different outcomes.

Other implementations of these and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The details of one or more implementations are set forth in the accompanying drawings and the description, below. Other potential features and advantages of the disclosure will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
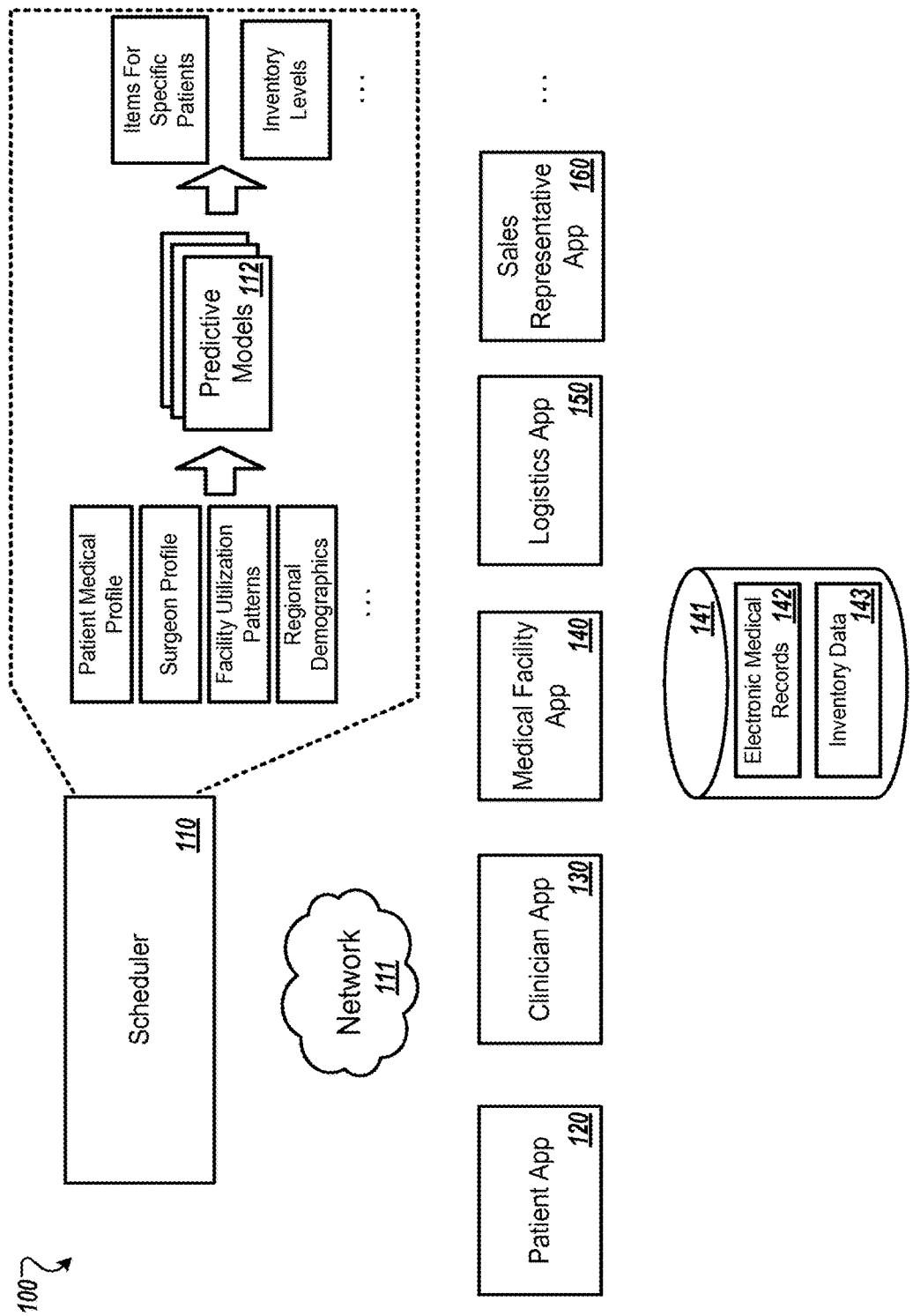
FIG. 1 is a block diagram that illustrates an example of a system for providing medical implants.

Referring to FIG. 1, a system 100 for predictive modeling of implant component needs includes a scheduler 110 that manages various aspects of planning for medical procedures. The scheduler 110 may be implemented as one or more computers, e.g., as a server system, that executes software modules configured to perform the management functions. Using a variety of types of information, the scheduler 110 can determine inventory levels that are appropriate for a particular medical facility, taking into account local demographics, hospital preferences, and other factors. The scheduler 110 also assists physicians and hospitals to, for example, schedule a new medical procedure and manage inventory so that needed supplies are available without requiring excessive inventory levels.

In some implementations, the scheduler 110 determines probabilities that different types and sizes of implants or other products will be utilized during the procedure for a particular patient. The scheduler 110 may generate ratings, determined based on a limited set of patient data, that indicate which items have the highest likelihood of being used for the patient's procedure. The probabilities indicating predicted needs for various scheduled procedures can be aggregated to determine a prediction of the overall set of items that will be needed by a medical facility. Using the predictions, the medical facility can maintain inventories that are likely to meet current needs, while avoiding the need to obtain and store inventory that is unlikely to be used. This can involve adjusting inventory by coordinating purchase, shipment, and delivery of items, and can also involve scheduling sterilization of tools and other pre-operative preparation. The scheduler 110 can also track a patient's compliance with a pre-operative plan or post-operative plan, as well as track patient outcomes over time and provide insight into the reasons for those outcomes.

The scheduler 110 communicates with other devices and applications over a communication network 111, which may include public and/or private networks and may include the Internet. For example, the scheduler 110 receives information about patient compliance with pre-operative and post-operative regimens from a patient app 120, and provides information to the patient app 120 for display to patients. The scheduler 110 also communicates with a clinician app 130, allowing physicians and nurses to enter information about patients and schedule new medical procedures. The scheduler 110 also provides information to medical facilities, such as hospitals and surgical clinics, using a medical facility app 140, which assists administrators and clinicians to make purchasing decisions and manage resources. Other apps and interfaces may also be provided, such as a logistics app 150 to communicate with common carriers and other logistics providers, and a sales representative app 160 to communicate with representative of medical device manufacturers and their representatives.

The functionality of the patient app 120, clinician app 130, medical facility app 140, logistics app 150, and sales representative app 160 may each be implemented as, for example, an application that resides on a client device, a server-side or web-based application, a web page or series of web pages, or another form of interface. The apps, 120, 130, 140, 150, 160 may be accessed using any appropriate client device, such as a desktop computer, a laptop computer, a cellular phone, a smart phone, a tablet computer, or a wearable computer.

To perform its various functions, the scheduler 110 may access information directly from the databases 141 of a medical facility. For example, the scheduler 110 may access and update patient data in electronic medical records. The scheduler 110 can also access inventory data 143 for medical facilities to determine whether inventory levels are appropriate and make recommendations.

To effectively coordinate medical procedures, the scheduler 110 employs predictive models 112 to predict or estimate which items will be needed to carry out individual medical procedures. Using information about particular patients, surgeons, and hospitals, the scheduler 110 predicts which items will be needed to carry out specific procedures for specific patients. The scheduler 110 may employ the predictive models 112 to generate predictions that take into account each patient's individual characteristics, resulting in probabilities that indicate how likely potential items and/or combination(s) of items for each patient's procedure.

For example, the scheduler 110 may automatically predict the appropriate sizes and types of implants needed for a particular patient's joint replacement surgery, based on the patient's height, weight, and/or other characteristics. Accordingly, if the scheduler 110 is used to coordinate a knee replacement surgery, the scheduler 110 can use the predictive models 112 to determine, for example, the two or three most likely implant sizes and the corresponding components to create the complete total knee. The calculations to predict a size and type of component based on patient data may be performed for each component of the prosthesis individually. Alternatively, after one component is selected or is determined to have a high probability of being used, then a list of associated components may be created based on the sets of components used together in prior procedures. Items that were used together previously can be predicted as being used together again. An approach combining both techniques may be used, in which some components are predicted based on patient data, and based on the prediction, one or more other components are selected to complement the set of components already predicted.

The scheduler 110 also uses the predictive models 112 to determine recommended levels of inventory that medical facilities should maintain. The predictive models 112 can provide predictions of inventory levels that are closely aligned with likely future needs, so that excessive inventory levels are avoided but items are also likely to be available when needed. The predictive models 112 can be trained to determine recommended inventory levels based on a variety of factors, including regional demographics, hospital preferences, surgeon preferences, and other factors. Training may use information about procedures performed at a specific facility of interest, at any of various facilities having similar characteristics, or general information about many different medical facilities. As a result of training, the predictive models 112 can provide inventory level estimates that are customized to the particular circumstances of each medical facility. For example, an inventory level determined for a specific hospital may be customized based on demographics in the area of the hospital, historical patterns of use of the hospital, the preferences of surgeons that operate at the hospital, and other factors. As a result, the scheduler 110 may provide inventory level recommendations that are tailored to the particular circumstances and characteristics of individual facilities. Further, from time to time, the inventory level for a facility change according to the predicted needs of the specific patients scheduled to be treated at the facility. For example, from week to week, a different inventory level may be determined, with a different quantity for each of various sizes of items being specified according to the set of patients scheduled to be treated during the current week.

The predictive models 112 can continue to be trained and updated over time. As more information becomes available, the predictive models 112 can become more accurate. Additionally, the training process allows the predictive models 112 to be responsive to changes and trends. As surgeon behavior and hospital usage change, continued training updates the predictive models to reflect these changes. For example, if surgeons at a hospital begin using more cruciate-retaining implants and fewer posterior stabilized implants, the predictive models 112 may recommend revised inventory levels that adjust general inventory accordingly. Similarly, the predictive models 112 may indicate that, for a particular patient, a cruciate-retaining implant is more likely to be used.

The predictive models 112 may be implemented in any of a variety of forms. For example, the predictive models 112 may be a set of rules, for example, rules, equations, or other expressions determined through regression analysis. For example, logistic regression may be used to generate a statistical or probabilistic model of a history of medical procedures. Various types of models may be used, including probabilistic, generative, or discriminative models. In some implementations, the predictive models may be trained using machine learning algorithms. Examples of types of machine learning models that may be used include maximum entropy classifiers, artificial neural networks, kernel machines, and support vector machines.

In some implementations, the predictive models 112 are generated so that each model corresponds to a single implant component or component type. For example, one model 112 may correspond to a cruciate-retaining tibial insert, another model 112 may correspond to a posterior-stabilized tibial insert, another model may correspond to a tibial tray, and so on. The models 112 may be further specialized, for example, to correspond to an implant component of a specific model or product series, a specific material or composition, for right-side or left-side use, and so on. Each of the models 112 may be configured to indicate a probability distribution for different sizes of its associated implant component. For example, the model 112 for the cruciate-retaining tibial insert can indicate the relationships needed to determine a probability distribution for the various sizes of the cruciate-retaining tibial insert. Thus, given a set of patient characteristics, such as height and weight, the model 112 can be used to produce a probability measure for each of the different sizes of a specific model of cruciate-retaining tibial insert.

The predictions that the scheduler 110 generates using the predictive models 112 may allow medical facilities to more closely align inventory levels with actual needs. By limiting inventory to items according to likelihood of use, a medical facility may significantly reduce the overall amount of inventory that is carried, which can significantly reduce expenses.

Managing inventory levels is often a challenge for hospitals and other medical facilities, as well as for medical device manufacturers. Hospitals have varying preferences for maintaining inventory. Some hospitals maintain an inventory large enough to cover every surgical possibility. Other hospitals prefer to operate with a very lean supply, and rely on sales representatives of medical device manufacturers to provide needed items. The sales representatives often spend a considerable amount of time coordinating the delivery of implants and instruments to operating rooms. To be able to meet potential needs of different hospitals, sales representatives often keep many sizes of implants on hand to cover every surgical possibility. This approach results in a vast inventory located in the field.

Inventory management is further complicated by the differences in populations served by different hospitals. A hospital's inventory needs are affected by the local demographics of the population around the hospital. For example, on average, males who have a knee replaced in central Wisconsin may be taller and may be of a different ethnicity than a male who has a knee replaced in southern Texas. As a result the inventory needs of hospitals in these two areas may be quite different. If a hospital's inventory is not customized for the local demographics, there may be large amounts of unused inventory.

Once implants and other items are provided to an operating room, surgeons and sales representatives are generally required to ensure compatibility of tools and implants provided. There are various reasons why components may not be used. For example, a component may have been recalled, or the component may be past its expiration date. As another example, a certain size or type of tibial baseplate may not be compatible with a particular size of femoral component, by design.

Tracking surgical outcomes and improving performance can also be a challenge. For example, the rates that patients are readmitted to a hospital after surgery are affected by a host of factors, including infections, pain, comorbidities, patient satisfaction levels, patients' failure to take medication or perform physical therapy, and so on. It is often difficult for hospitals and doctors to track patient compliance with pre- and/or post-operative regimens, and to record surgical events, such as blood loss volume, whether a tourniquet was used, etc. As a result, it is often difficult to identify unfavorable trends and eliminate the causes of poor outcomes. In many instances, insurance providers reimburse doctors for only a limited number of post-operative visits, so there is an incentive for surgeons and hospitals to achieve favorable outcomes. However, it may be difficult for surgeons and hospitals to determine which factors contributed to the outcomes observed, and to identify and implement measures to improve performance.

Figure 2:
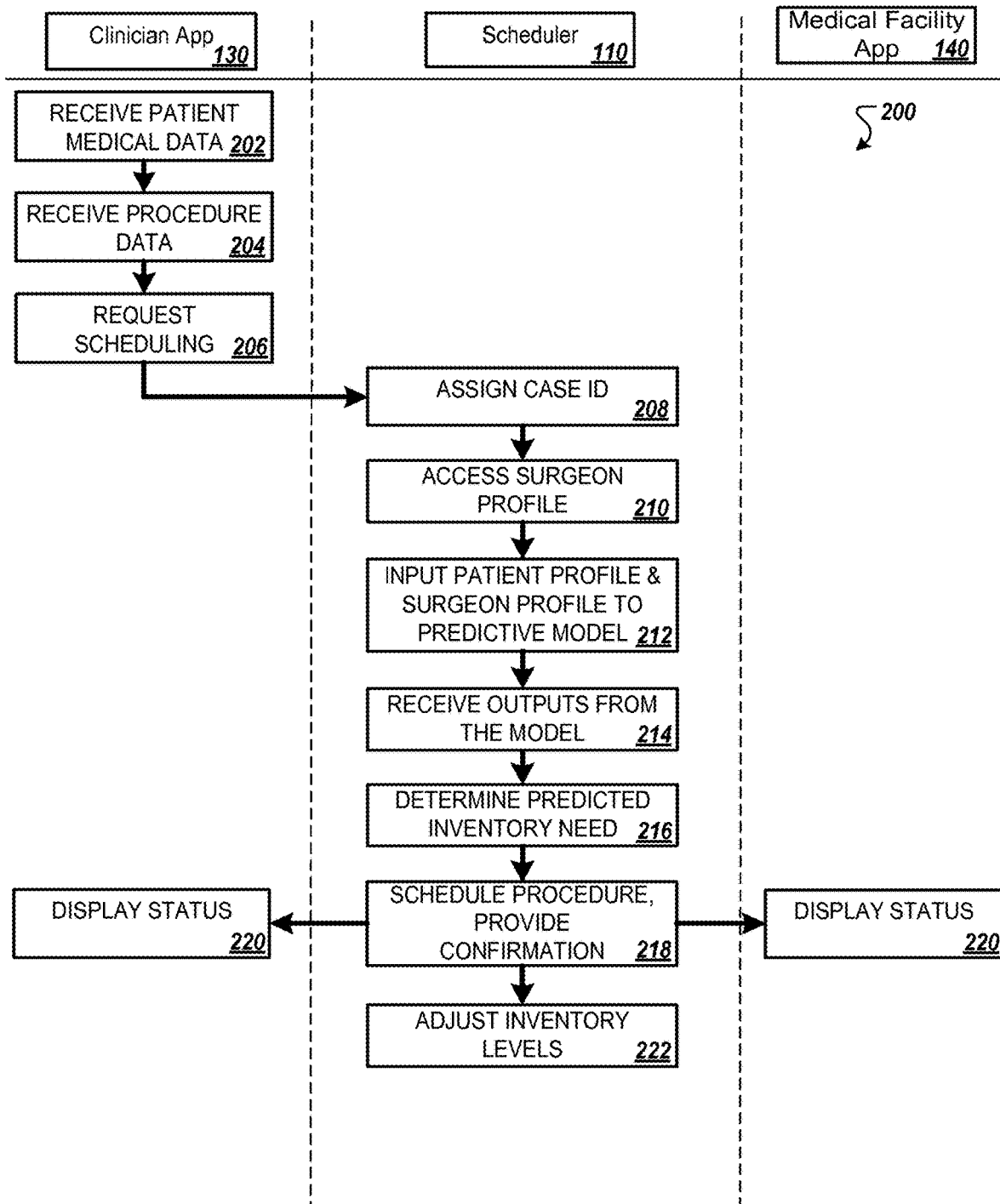
FIG. 2 is a diagram that illustrates an example of a process for scheduling a medical procedure.

Referring to FIG. 2, a process 200 for scheduling a medical procedure involves interactions between the scheduler 110, the clinician app 120, and the medical facility app 140. In the process 200, a user, such as a clinician, hospital employee, or someone working on behalf of a healthcare professional, requests that a new medical procedure be scheduled. The scheduler 110 determines probabilities that various items, such as implants, sub-components of an implant system, or instruments, will be needed to carry out the procedure. The scheduler 110 also locates the needed items and adjusts the inventory of the medical facility to make sure that the needed items will be present at the scheduled time of the medical procedure.

In further detail, at step 202, a user enters a patient's medical data using the clinician app 130. For example, during a patient consultation, a nurse or physician may enter patient characteristics into the clinician app 130 using a tablet computer, laptop computer, desktop computer, or other device. The patient medical data may include, for example, the patient's height, weight, age, sex, race, body mass index (BMI), and/or other characteristics. The patient medical data may also indicate comorbidities, for example, diseases or conditions in addition to the condition to be treated. In some implementations, the clinician app 130 accesses stored medical records for the patient to obtain patient medical data. Information about the medical characteristics of the patient is referred to generally as a patient profile.

At step 204, the user uses the clinician app 130 to enter information about a medical procedure to be performed for the patient. The information may indicate the type of procedure, the date of surgery, the surgeon or other members of the medical team, the location that the procedure is to be performed, and so on. For example, for a knee replacement procedure, the clinician may provide input that indicates that a total knee replacement will be performed and whether the procedure is on the right or left knee. The information may also indicate other details, such as whether the procedure involves an implant that is posterior-stabilized, cruciate-retaining, or varus/valgus constrained.

At step 206, the user uses the clinician app 130 to request scheduling of the patient's procedure. The medical data for the patient, the procedure information, and the scheduling request are transferred to the scheduler 110 over the network 111. The information may also be transferred to the electronic medical records of the hospital or other medical facility where the medical procedure will be performed. The scheduler 110 may also obtain the data from electronic medical records stored at the medical facility or a remote location.

At step 208, the scheduler 110 responds to the scheduling request by assigning a case identifier ("case ID") for the patient's medical procedure. The case ID is associated with the patient medical data and procedure data to designate the information as corresponding to the particular procedure being scheduled. The case ID may be assigned so that it distinguishes the particular procedure from other procedures performed at the medical facility. In some instances the case ID may be unique among all the procedures scheduled by the scheduler 110.

At step 210, the scheduler 110 accesses a surgeon profile that includes information about the surgeon that will perform the medical procedure. The surgeon profile indicates information about the surgeon's preferences and technique. The surgeon profile may include explicit preferences that the surgeon has indicated, for example, in answers to a questionnaire or data entered in an electronic form. For example, a surgeon may indicate that a specific make, model, or type of implant is preferred. Similarly, the information may indicate that a surgeon prefers to have available during surgery implants that are one size greater and one size smaller than the indicated size, or that the surgeon prefers to have implants that are one size and two sizes larger and smaller. The surgeon profile may include information inferred from records of the surgeon's prior procedures. For example, the surgeon profile may indicate a make, model, or type of implant that the surgeon typically uses, along with the frequency or likelihood of use, as determined from the surgeon's history of prior procedures.

The surgeon profile may include a variety of other information. For example, the surgeon profile may indicate information such as how many of the surgeon's prior procedures used cruciate-retaining implants, posterior-stabilized implants, and other types of implants or other items. For example, the surgeon's prior procedures can be compared with records of surgeries performed by other surgeons. The surgeon profile may indicate whether a surgeon typically uses implants that are smaller than, larger than, or the same size as the implants typically used by other surgeons. This information may reflect, for example, that patients having certain characteristics or combinations of characteristics are treated in a certain way. For example, when a patient's anatomy is in between two sizes of implants, some surgeons select the smaller size, and other surgeons select the larger size. The surgeon profile can indicate which decision the particular surgeon typically makes when a patient's anatomy is in between sizes. The surgeon profile may also reflect the surgeon's typical treatment for specific types of patients.

In some implementations, the scheduler 110 has access to data storage that includes stored surgeon profiles for multiple different surgeons, including surgeons affiliated with different hospitals and geographical areas. The scheduler 110 identifies the surgeon involved in the procedure to be scheduled and accesses the corresponding surgeon profile, for example, using the surgeon's name or a surgeon identifier received from the clinician app 130.

In step 212, the scheduler 110 inputs information from the patient profile and information from the surgeon profile to one or more of the predictive models 112. The predictive models 112 are configured to indicate items likely to be needed for the procedure, for example, which implants, instruments, or other supplies should be provided in the operating room at the time of surgery. The predictive model 112 has been trained to make the prediction based on patient characteristics such as height, weight, age, and so on of the particular patient receiving the procedure. The predictive models 112 may have been trained using data indicating which items were previously used in procedures for patients having characteristics similar to those of the current patient. Through training, the predictive models 112 have been adjusted to reflect correlations between patient characteristics and the use of specific items, allowing the useful predictions to be provided.

The predictive models 112 may also be configured to use information about the surgeon to generate predictions. The information from the surgeon profile that is input to the predictive models 112 allows the predictive models to indicate items according to the preferences and history of the particular surgeon performing the procedure. Accordingly, if the surgeon has a particular history of using implants that are slightly larger than average, the predictive models 112 may provide predictions that show that the larger implants are likely to be used in the current procedure. The predictive models 112 may have been trained using data indicating the prior procedures of many different physicians, allowing the model to learn how different surgeon characteristics and preferences affect the need for medical supplies. In some implementations, the predictive model 112 has additionally or alternatively been trained using information about the history of the particular surgeon associated with the current procedure being scheduled.

In step 214, the scheduler 110 receives output from the predictive models 112. The output indicates one or more items that are likely to be needed for the particular patient. Since the outputs are determined by the predictive models 112 using the patient profile and surgeon profile, the information may be customized for the particular combination of patient characteristics and surgeon characteristics associated with the procedure. The output can indicate components that are likely to be appropriate for the patient's anatomy, and that are also likely to meet the surgeon's preferences. As discussed further below, the output of the predictive models 112 may indicate the likelihood that different components will be needed. For example, the predictive models may provide probability scores or other values that indicate the relative likelihood that different components will be needed.

In some implementations, the output of the predictive models 112 includes probability scores for each of various potential items, where each probability score indicates the estimated probability that the corresponding item will be used in the procedure. As an example, for a knee replacement procedure, a probability score may be provided for each of the possible sizes of femoral components that may be implanted. Probability scores may be provided for different sizes and/or types of tibial components, instruments, and any other items that may be needed. In this manner, the predictive models 112 provide probability distributions that can be used to determine whether the medical facility's available inventory is sufficient to meet the needs of the procedure, and to make adjustments to the inventory level if needed.

The output of the predictive models 112 may indicate probability scores for multiple items that can be used together to complete the procedure. For a joint replacement procedure, a prosthesis may include multiple different components that must mate together, or work in concert with each other, according to the design limitations or specifications of the particular design indicated by the manufacturer of implant. The output of the predictive models 112 may indicate each of the different components needed, resulting in a set of interoperable components that can form a complete and functioning prosthesis that meet interoperability requirements that the manufacturer or other party has set for the implant system. For example, if a knee replacement involves a femoral component and a tibial component, the output of the predictive models 112 may indicate components from the same manufacturer and product series, having sizes that are compatible for implantation together. The output may also indicate other supplies, such as specific sets of instruments and trials to be used during the procedure. When the predictive models 112 are trained or otherwise generated, compatible combinations of components may be inferred from examples of prior procedures that have been performed. In addition, or as an alternative, the predictive models 112 may include or be trained using compatibility rules that specifically identify appropriate combinations and/or inappropriate combinations. For example, compatibility rules may indicate that only components from the same manufacturer or product series may be used together in a prosthesis.

The predictive models 112 may be configured to make predictions with any of various different levels of specificity. In some implementations, the predictive model 112 indicates which items are needed in a manner that allows the precise item, including size, to be identified. For example, the output of the predictive models 112 may correspond to particular part numbers, SKUs, model numbers, or product codes. In this manner, the output of the model can indicate a type, make, model, size, or other details needed to identify the particular item needed. In some implementations, the predictive models 112 may provide more general indications of items to be used, for example, by specifying a product series of an item without specifying a size, or by specifying simply a type of item and manufacturer.

In some implementations, the predictive models 112 may use image data or data derived from imaging data to generate its outputs. For example, a patient profile can be supplemented with an X-ray image, magnetic resonance imaging (MRI) image, computed tomography (CT) image and input to the predictive models 112. As another example, scores or features extracted from an image may be provided. As another example, a classification based on image data, or the results of an automated templating system may be provided to the predictive models 112. Information from imaging data, combined with the patient profile, may be used to provide improved estimates. The predictive models 112 may be trained using imaging data as well as the information in the patient profile. For example, a data set can be compiled that includes pre-operative imaging data for a set of patients and data indicating supplies, such as sizes of implants, used in the procedures for those patients. Based at least in part on the patterns of items used and corresponding image data, regression techniques and other training methods may be used to train the predictive models 112 to use imaging data as a factor in predicting which items are likely to be used for future patients.

In step 216, the scheduler 110 uses the outputs of the predictive model to determine a level of inventory needed for the medical facility. For example, the scheduler 110 may aggregate probability scores for the particular procedure being scheduled with probability scores for other procedures to predict the overall level of inventory needed for the medical facility. For example, when a new knee replacement procedure is being scheduled, information about the probabilities that various sizes of knee implants will be used may be combined with information that indicates the probabilities that those sizes of knee implants will be used in other knee replacement procedures that are already scheduled. The probability distributions for the various patients may be used to determine a prediction of how many of each size of knee implant will be needed at the medical facility. The estimate of the overall inventory need of the medical facility may be determined for a specific time period, such as over the next week, month, or quarter, or may be performed for a set of procedures of a particular type, or for all scheduled procedures.

The scheduler 110 may compare the predicted inventory needs for the medical facility with the actual inventory for the medical facility. Based on the comparison, the scheduler 110 may determine whether items likely to be needed for the procedure being scheduled will be available. For example, if certain knee implants are likely to be used in the procedure, and a hospital does not have a sufficient quantity of the needed sizes of implants, the scheduler 110 can identify the items and quantities needed. This information may then be provided to the hospital so that the inventory levels may be adjusted to meet the predicted needs.

In some implementations, the probability scores received in step 214 are provided as input to another predictive model 112 along with the probability scores of other patients whose procedures have been scheduled. The predictive model 112 may use the probability scores for multiple different procedures, e.g., procedures of multiple different patients, to determine the overall inventory need for the medical facility.

The predictive model 112 may also receive a medical facility profile that indicates characteristics or preferences of the medical facility. For example, the medical facility profile may indicate a number of operating rooms available for different types of procedures or on particular days, numbers and types of instrument sets available, or sterilization preferences, such as whether flash sterilization is permitted or not and an overall time required to collect used instruments, sterilize them, and return them for use in another procedure. Using this information, the predictive model 112 can determine, for example, likelihoods that instruments, operating space, staff, and other needs can be met at various times. For example, although an operating room may be available at a particular day and time, instruments needed for a particular procedure may not be available because the instruments are needed for another procedure scheduled for the same time. Similarly, even if the instruments are not scheduled to be used at the same time, the instruments may not be available because they are being sterilized after use in a prior procedure. By taking into account these factors, the predictive model may indicate probabilities that operating room space, instruments, and other needs will be available, so that a procedure can be appropriately scheduled.

At step 218, the scheduler 110 completes the scheduling of the procedure. The scheduler 110 may use information generated in step 216 to identify days, times, and locations that are suitable for carrying out the procedure. For example, the procedure can be scheduled for a time when an operating room is available, instruments predicted to be needed are available, and the physician and other staff are also available. In some implementations, the scheduler 110 takes into account physician preferences, for example, by scheduling surgeries performed by a particular surgeon on the same day rather than different days, or by scheduling procedures with a desired sequence or timing.

The scheduler 110 updates the records of the medical facility to show the date and time scheduled for the procedure, along with any other information about the procedure that may be needed. The scheduler 110 may reserve a physical space, such as an operating room, within the medical facility for carrying out the procedure. The scheduler 110 also notifies the clinician and the medical facility of the status of the scheduled procedure. If the predicted inventory needs determined in step 216 exceed the inventory of the medical facility, the scheduler 110 provides a warning or other indication that additional items are needed.

At step 220, the clinician app 130 and the medical facility app 140 display status information provided by the scheduler 110. For example, a confirmation indicating that the procedure has been successfully scheduled may be displayed. Information about which items are predicted as likely to be used, and whether those items are likely to be available, can also be provided. If the procedure cannot be scheduled for some reason, for example, if there are no available operating rooms at the desired day or time, or if items needed for the procedure may not arrive by the desired date, that information is displayed.

At step 222, the scheduler 110 adjusts inventory levels at the medical facility. When the predicted inventory needs of the medical facility exceed the actual inventory, the scheduler 110 may cause additional items to be ordered. For example, the scheduler 110 may generate an order to purchase items needed to bring the inventory up to the predicted level of need. The scheduler 110 may adjust inventory automatically as the predicted needs change, or may indicate recommended adjustments for approval by employees of the medical facility. The various actions that the scheduler 110 may perform include ordering items, expediting delivery of previously ordered items, requesting items from another medical facility, and requesting that a manufacturer manufacture items. When inventory levels at the medical facility exceed predicted needs, the scheduler 110 may make adjustments that reduce inventory levels, for example, by delaying or cancelling orders or shipments, returning excess products to vendors, or sending excess products to other medical facilities or other parties.

The scheduler 110 may verify prices of items when items are purchased. As inventory at a medical facility is depleted and new orders are created, the scheduler 110 may check each purchase against appropriate price lists and contractual agreements to verify that the medical facility is charged an appropriate price. Medical device companies often have many different price lists with different product costs, and hospitals may have many different contractual prices with different manufacturers and vendors. By automating the verification of pricing, errors that may be caused by manual ordering can be avoided, along with the significant loss of time to correct the errors.

In some implementations, the scheduler 110 performs price checking by accessing a table, spreadsheet, or other data that indicates prices corresponding to a stock keeping unit (SKU) or other product identifier. When preparing a purchase order or performing a transaction, the scheduler 110 determines the identifier for the product being purchased, looks up the approved price, and compares the approved price to the price of the current transaction. If the price offered is more than the approved price, then the scheduler 110 may modify the transaction to reflect the approved price or cancel the transaction and obtain the item from another vendor. In some implementations, the scheduler 110 checks prices of items using a plug-in module or service provided by a third-party.

The scheduler 110 may re-calculate the overall inventory needs of the medical facility from time to time, for example, each time a procedure is scheduled or performed, when products are used and inventory is decreased, or at a regular interval, such as once per day. The set of scheduled procedures changes over time, and as a result, inventory needs are predicted based on the item use probability scores of different sets of procedures at different times. The combination of the projected needs for all the scheduled procedures can be used to generate predictive demand curves, which may be monitored to ensure compliance with the medical facility's inventory management policies.

The scheduler 110 can take into account various timing constraints when adjusting inventory levels. In addition to estimating overall inventory levels needed over a given time period, such as the next week or month, the scheduler 110 can address the supply needs of each scheduled procedure individually. The scheduler 110 can take into account the date that each individual procedure is scheduled to occur, and cause supplies needed for various procedures to be stocked in advance of their respective scheduled dates. As surgeries occur and inventory levels change, the inventory levels may be re-assessed and adjusted to meet the needs of each individual procedure that is scheduled to occur.

To assist in calculating how far in advance items should be ordered, the scheduler 110 can store data indicating time periods required to obtain items from different vendors, manufacturers, or locations. The data may indicate delivery periods, for example, windows of time that should be allocated to allow ordered items to arrive at the medical facility. A delivery period may be, for example, a time period in which it is expected that deliveries will arrive with at least level of confidence, e.g., 80%, 90%, or 95%, or may be a time period in which delivery is guaranteed by the carrier. At a certain time before each procedure, for example, at a time that precedes the schedule procedure by the delivery period or slightly more than the delivery period, the scheduler 110 can make a final determination of which items should be ordered, if any, to arrive in time for the procedure. As a result, the scheduler 110 may delay purchases until soon before the surgery, while still having items delivered by the scheduled times.

As an example, a particular procedure may be scheduled three weeks in advance of the date that surgery will occur. An estimate of supplies likely to be needed for the procedure may be predicted the same day the procedure is entered into the scheduling system. As the scheduled date approaches, the scheduler 110 may repeatedly re-evaluate the inventory levels that will be available on the scheduled date to determine whether the needed items will be available. The scheduler 110 may also access data indicating, for example, a shipping time needed for delivery from a supplier. Shipping times may be different for different types of items, for items from different suppliers, for items shipped from different locations, and so on, and the scheduler 110 may maintain records of these different shipping times. The scheduler 110 may determine that for needed implant components, five days should be allowed for delivery. Based on this shipping time, the scheduler 110 may make a final determination six days before the procedure whether the medical facility's inventory lacks an appropriate quantity of any implant components likely to be needed. If any components are needed, the scheduler 110 then orders the components, which provides sufficient time to receive the shipment and use them in the upcoming procedure. The scheduler 110 may provide shipping and delivery instructions with the order to cause the ordered items to be delivered in the appropriate time.

In some instances, waiting to order items can improve efficiency. For example, after scheduling a first procedure, a previously scheduled procedure may be cancelled or re-scheduled, making components available for the first procedure that would not have been considered available previously. Thus delaying the ordering items of items can avoid excess purchases of components and facilitate efficient use of items already in inventory.

After a particular procedure is scheduled as shown in FIG. 2, the scheduler 110 periodically confirms the status of the planned procedure, and also verifies that the needed items will be available. For example, if a surgeon makes changes to the surgical plan or updates data about the patient, the scheduler 110 may generate a new prediction of probabilities regarding which items are needed. These new probabilities are used to update the prediction of needed inventory at the medical facility, and the inventory is adjusted accordingly. As another example, a procedure may be changed if, for example, a patient does not meet pre-operative medication or physical therapy goals, if an operating room becomes unavailable, or if the procedure is rescheduled for another day. In each of these instances, the scheduler 110 may take action to ensure that all items indicated as likely to be needed for the procedure will be available according to the revised plans. For example, after revising the schedule for the procedure, the scheduler 110 may determine that there is an unreasonable likelihood that needed items may not arrive in time for the procedure under the prior shipment plan. As a result, the scheduler 110 may procure items from a different source, or alter shipment dates or the mode of shipment to expedite delivery and meet the requirements of the procedure.

In some implementations, the scheduler 110 selects particular items for the procedure based on the outputs of the predictive models 112. Thus, the scheduler 110 may determine which items should be provided for a particular patient and procedure without the clinician indicating which items should be provided, and without size templating or imaging of the patient's anatomy. The scheduler 110 may apply a set of rules to the outputs to finalize a set of items that will be designated as required for the procedure. The outputs of the predictive models 112 may indicate probabilities for different alternatives, such as likelihoods for different implant sizes when only a single size of implant will actually be implanted. To select from among various alternatives, the scheduler 110 may apply one or more thresholds so that appropriate items are selected. In some implementations, items that have at least a minimum likelihood of being used are selected. In some implementations, the most likely items are selected until a total probability is reached, for example, a set of items are selected whose combined likelihood scores meet a threshold, or are within a predetermined range. That is, items may be selected so that it is known, within a particular level of confidence, such as 70%, 80%, 90%, that the implant components that will be used for the patient are in the selected set.

In a similar manner, and as discussed further below, the outputs of the predictive models 112 for each of multiple different scheduled procedures can be used to determine quantities of items that will permit a medical facility to meet the needs for each of the scheduled procedures. For example, each of the scheduled procedures for a particular time period, e.g., a particular day, week, or month, can be identified. A probability distribution indicating which items, including which implant components in various sizes, can be determined for each individual scheduled procedure. For example, for each total knee replacement procedure during a particular week, a probability distribution can be determined to show the probability that each size of posterior-stabilized femoral component will be needed. From the probability distributions for different procedures and different types of items, an overall distribution can be determined to indicate a quantity for each size of each of the various items likely to be needed during the time period. For example, the distribution can include a different quantity of a first implant component, such as a particular model of cruciate-retaining tibial insert, for each of the different sizes in which the first implant component is made, or at least for those sizes likely to be needed.

The quantities can be determined to provide at least a minimum level of confidence of meeting the needs of the medical facility over the time period, while also limiting excess amounts of inventory being required. For example, based on various constraints or preferences, a medical facility may set a desired confidence level at which to hold implant components in inventory. That confidence level may represent a predetermined likelihood, e.g., 80%, 90%, 95%, 98%, or another value, that items will be available for a given procedure or set of procedures. Then, the quantities of items to be provided can be calculated to meet that predetermined confidence level. For example, when a facility has set a 95% target confidence level, a quantity of cruciate-retaining femoral components of a particular size can be calculated so that having that quantity on hand will give a 95% likelihood that each of a set of scheduled procedures will have that component available if needed. In particular, to maintain efficiency, the quantity determined can be the smallest quantity that still allows for the minimum confidence level for availability at the medical facility. The confidence level may be determined based on outputs of the predictive models 112. Confidence levels indicating the probability that a quantity of items will be sufficient for a set of scheduled procedures may be determined for individual sizes of components, for component types, combinations of different items, or for an inventory as a whole. In addition, or as an alternative, confidence levels may be determined by looking at historical data sets of past surgeries, e.g., to determine whether the selected quantities would be sufficient for representative samples of previous patients having similar characteristics to those scheduled to be treated.

The quantities can be determined to meet the desired confidence level without including excess beyond what is needed to achieve that confidence level, or at least without excess beyond a predetermined maximum amount. This can improve efficiency by avoiding the overhead of providing large amounts of items that are not likely to be used. For example, the quantities may be determined to provide a confidence level for availability that is a particular value, e.g., 95%, or a within a range, e.g., between 90% and 98%. The quantities can be determined so that the corresponding confidence is bounded, e.g., less than a pre-selected upper threshold, to appropriately balance the ability to meet patients' anticipated needs with the use of resources to obtain and store inventory. As a result, the quantities of implant components may be determines so that they do not exceed a level needed to achieve the minimum confidence level by more than a predetermined maximum excess amount. This excess amount may be selected as, for example, a percentage of the quantities determined or as a number of items, or may be set at zero to require quantities to be as close as possible to the quantities needed to obtain the desired level of confidence. In instances where the determined quantities are generated to include a safety stock level or other minimum level, the maximum excess amount may be the safety stock level or other minimum level or buffer amount. As an example, the scheduler 110 may determine, based on analysis of the probability distributions generated for individual patients, that, for a set of surgeries scheduled for a particular week, a quantity of 7 cruciate-retaining tibial components of size 4 is the smallest quantity that will provide at least a desired 95% confidence of this component being available for each of the surgeries in the set. A safety stock level for the component may be determined, which may be a policy that at least 2 of the particular component should be stocked at all times. As a result, the scheduler 110 may indicate that, for the time period that includes the set of surgeries, a quantity of 9 size 4 cruciate-retaining tibial components that should be held in inventory.

In some implementations, the scheduler 110 may locate, and in some instances reserve, the items that have been selected for a particular procedure. The scheduler 110 may access data indicating inventory at a variety of different locations, for example, current inventory of the medical facility, contents of shipments in transit to the medical facility, items in nearby medical facilities, or items in stock with sales representatives, manufacturer's distribution centers, or third party vendors. After locating the items needed for the procedure, the scheduler 110 designates the items for use in the procedure. The items, whether located at the medical facility or in another location, are associated with the case ID or other identifying information, and the items are reserved for the specific procedure. For example, if the items are present in inventory at the medical facility, the items may be virtually tagged with information such as the case ID, surgeon ID, date and time of surgery, or other information.

The scheduler 110 may tag and reserve a specific instance of an item for use in the procedure. For example, the inventory of the medical facility has three identical implants, e.g., three instances or copies of the same implant, all having the same part number. However, the three distinct instances of the implant may have unique serial numbers or tracking numbers assigned, e.g., with bar codes or other optical codes, radio-frequency identification (RFID) tags, markings, etc., to distinguish one from the other. The scheduler 110 may designate a specific one of the three identical implants for use in the medical procedure, and may store data that associates the case ID with the corresponding unique tracking number. Tracking numbers may be associated with records for items in an inventory database, and also be physically linked to the actual items, for example, through a bar code, RFID tag, or other tracking device affixed to the item or the item's packaging. As items are moved from one area to another, the tracking devices are scanned and the times and locations of the scans are recorded. As a result, inventory records may include a log of the movement of items, including the location of the most recent scan which generally indicates the current location of the item. In general, whenever the scheduler 110 reserves an item for a procedure, the scheduler 110 may reserve a specific instance or copy of the item, for example, by reference to its unique tracking number which distinguishes it from other identical copies of the same item.

In some implementations, the scheduler 110 may simply reserve items according to type, for example, using a part number or model number without designating a specific instance. Some types of items may be reserved without a specific tracking number, while a specific instance and tracking number may be reserved for other types of items. As an example, small, common, or inexpensive items, such as gauze pads, may be reserved according to the general characteristics, without indicating a specific one of the many identical gauze pads, and optionally without designating a manufacturer or part number.

Once assigned to the particular procedure, the reserved items are deducted from the available inventory so that they cannot be assigned to or used in any other procedure. To manage the inventory, the medical facility may have a database storing records of each physical item in inventory. Each physical item in inventory may have a unique item identifier used for tracking purposes, such as a serial number or other identifier. The item identifier may be encoded in a bar code, RFID tag, or other tracking device. The scheduler 110 interacts with a medical facility's inventory management system to update the inventory records, causing the case ID to be linked to the item identifier in the inventory system's records.

In some implementations, a manufacturer uses predictions of which products and quantities should be available for future medical procedures. The item use probability scores for scheduled procedures of various individuals can be combined to predict quantities of items needed at particular medical facilities over a period of time. As discussed above, the probability scores may be generated based at least in part on patient characteristics such as age, sex, height, and weight. The predicted quantities of items for multiple medical facilities may be aggregated to determine needed quantities for a particular region, such as a region served by a manufacturer's distribution center. Based on the predicted need for the region, the manufacturer can adjust the level of inventory that is stocked at the distribution center. In addition, the manufacturer can use predicted quantities needed for multiple medical facilities or multiple geographical regions to set production levels. For example, the manufacturer can adjust the quantities produced for various sizes of implant components to meet an aggregate level of demand predicted.

The predictions used by manufacturers may be based on records of upcoming medical procedures, which allows manufacturers to tailor distribution and production according to the needs of the specific set of upcoming procedures. With predictions based on the set of procedures scheduled to be performed in given period, for example, the next week, month, quarter, and/or year, manufacturers can dynamically adjust production levels to meet the predicted need. Production, as well as shipping to distribution centers and medical facilities, may be performed on a "just-in-time" or an as-needed basis in order to meet inventory needs while avoiding excess production or distribution. The scheduler 110 or multiple such systems may produce estimates for multiple medical facilities or geographical regions, and update the estimates periodically, for example, hourly, daily, weekly, as procedures are completed or newly scheduled, etc. The scheduler 110 may provide these estimates to one or more manufacturers, which then change production quantities, production schedules, and distribution plans to match the predicted levels of need.

Figure 3A:
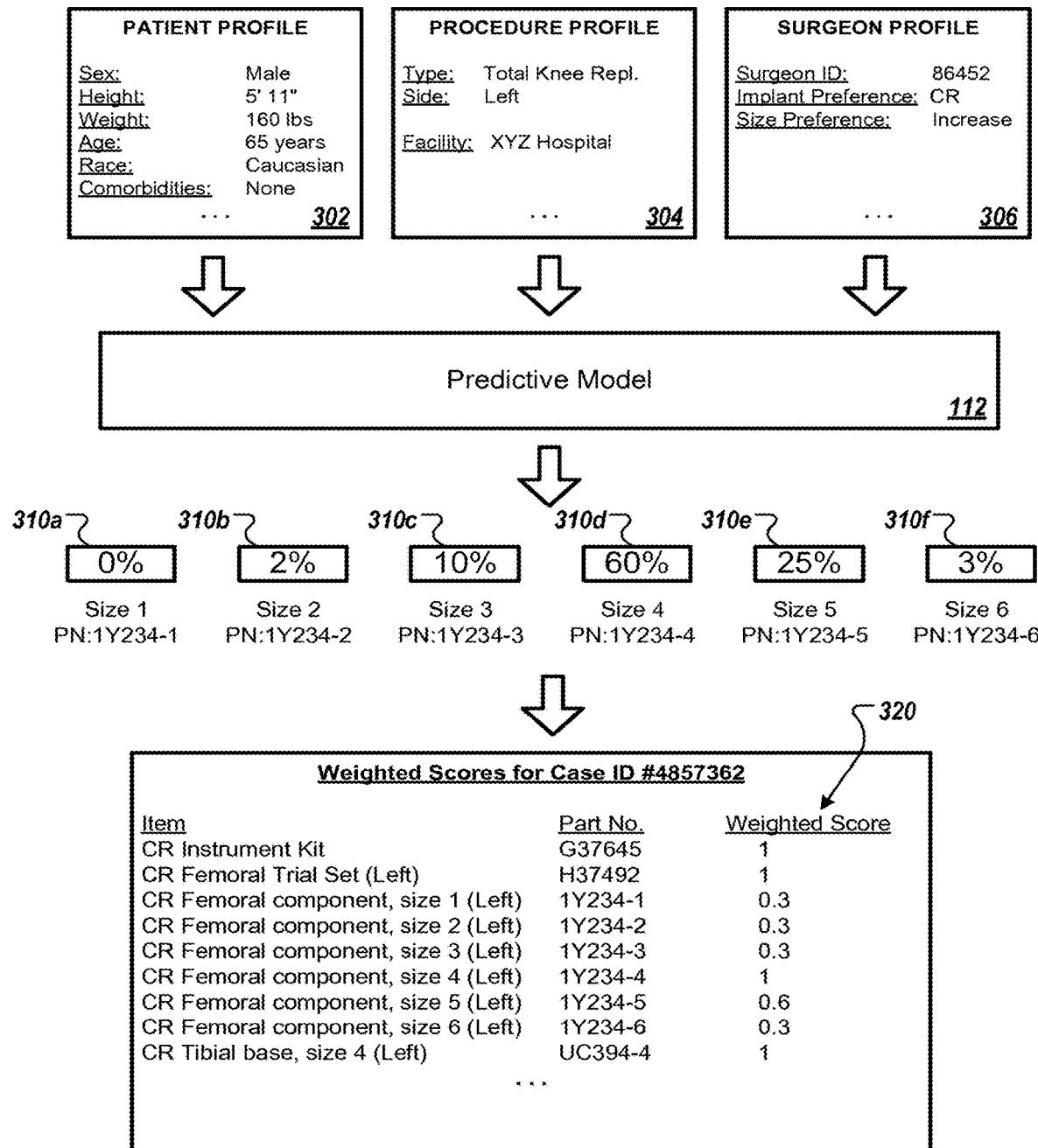
FIGS. 3A through 3D are diagrams that illustrate examples using predictive models.

Referring to FIG. 3A, a more detailed example of using a predictive model 112 is shown. In the example, the scheduler 110 uses information about a patient and other information to predict the items that should be provided for a total knee replacement for the patient.

The input to the predictive model 112 includes a patient profile 302, a procedure profile 304, and a surgeon profile 306. The patient profile 302 includes physical characteristics of the patient, for example, sex, height, weight, age, race, and comorbidities. Additional patient characteristics, such as BMI, or fewer patient characteristics may be used. The procedure profile 304 indicates the type of surgery (for example, total knee replacement), whether the surgery is on the right knee or left knee, and the hospital where the surgery will take place. The surgeon profile 306 indicates the surgeon who will perform the surgery, a preference of the surgeon to use cruciate-retaining (CR) implants, and a preference of the surgeon to increase size if a patient's anatomy is between two sizes of implants. In addition, a surgeon may also desire to have a "back up" system available in case a decision is made intra-operatively to change from a CR system to a posterior stabilized (PS) system. When the surgeon's history or preferences indicate a desire to have PS implants available, the predictive model 112 would also determine probability scores and potential demand for PS knee implant products as well.

The degree to which the inputs affect the output of the predictive model 112 may vary based on the data used to generate or train the predictive model 112. For example, some patient characteristics may be more strongly correlated with implant sizes than others. For example, height and sex may be more indicative of implant size than age and weight. The parameters that define the predictive model 112 are learned or derived from the training data set, and so the predictive model 112 reflects the various relationships that exist in the training data set. In some implementations, the process of training or generating the predictive model 112 may reveal which inputs or combinations of inputs most strongly or most accurately suggest implants that are needed. The predictive model 112 may naturally assign greatest weight to these parameters. In some implementations, if a subset of patient characteristics are known to be highly predictive, then the predictive model 112 can be configured to provide output based on only those characteristics. For example, only the two or three patient characteristics that have the most predictive influence over implant selection may be input to the predictive model 112. In some instances, the predictive model 112 can be configured to predict likelihoods that certain implant components and sizes will be used based only patient physical characteristics such as height, weight, age, and sex, without information derived from imaging the patient's anatomy and without a clinician indicating an expected implant size.

In the example of FIG. 3A, the predictive model 112 provides outputs 310a-310f that indicate likelihoods that specific items will be used in the procedure. The set of outputs 310a-310f may represent a probability distribution or probability curve indicating the likelihood of use across a range of products, in this instance, different sizes of a particular model of femoral component, e.g., femoral component model "1Y234." This particular model of femoral component comes in a variety of different sizes, e.g., sizes 1 to 6. Each output 310a-310f illustrated corresponds to a particular model and size of femoral component. For example, each output 310a-310f may correspond to a different part number. The output 310a, for example, corresponds to a cruciate-retaining femoral implant with part number "1Y234-1," which has a size of 1. The outputs 310a-310f indicate that, given the particular combination of patient and surgeon characteristics input to the predictive model 112, there is a predicted 0% likelihood that a size 1 femoral component will be needed, a 2% likelihood that a size 2 femoral component will be needed, a 10% likelihood that a size 3 femoral component will be needed, a 60% likelihood that a size 4 femoral component will be needed, a 25% likelihood that a size 5 femoral implant will be needed, and a 3% likelihood that a size 6 femoral implant will be needed.

The predictive model 112 may provide an output for each item in a set or catalog of items that the predictive model 112 is trained to predict. For example, if there are ten sizes of femoral components for cruciate-retaining implants, and ten sizes of femoral components for posterior stabilized implants, the predictive model 112 may output twenty different scores, with each score indicating the probability that a corresponding implant will be needed. When the input to the predictive model 112 indicates that a cruciate-retaining implant system will be used, the outputs for each incompatible implant, such as posterior stabilized implant components, may indicate a very low or zero probability.

The predictive model 112 may determine probabilities of use for other items in the same manner as the femoral components. For example, probability scores for tibial bases and tibial inserts may also be generated. Similarly, the scheduler 110 may also indicate probabilities for sets of trial components designated for use with the selected femoral components, tibial bases, and tibial inserts, or individual trial components which may be re-usable or disposable. The trials may be full or partial sets of trial components. Probability scores for the use of appropriate instrument sets for completing the procedure may also be selected, as well as sutures, tourniquets, antibiotics, and other supplies.

In some implementations, the predictive model 112 may be trained with data indicating the sets of instruments and supplies used in or provided for use in various prior procedures. The training data may include information about prior surgeries performed by the same surgeon or performed at the same hospital as those indicated by the input to the predictive model 112, allowing the model to provide a prediction customized based on the actual history of use by the surgeon and/or hospital. Thus if a particular surgeon tends to use fewer sutures than other surgeons, or if the hospital tends to provide a larger range of supplies than other hospitals, the predictive model 112 may provide predictions that are consistent with these patterns. Even if the model 112 has not been trained using data that indicates usage of the particular surgeon and hospital, the predictive model 112 may still predict which items are needed. The predictive model 112 may reflect relationships between the usage of various items and patient characteristics, surgeon preferences, procedure characteristics, where the relationships have been learned from data about procedures performed by other surgeons at other hospitals.

As shown in FIG. 3A, the outputs 310a-310f, which indicate probability of use estimates, may be used to determine weighted scores 320. The weighted scores 320 can represent a level of demand for particular items, determined based on the probabilities of use. For example, each of the outputs 310a-310f may be mapped to a weighted score 320 that represents an estimate of a quantity of each item to be stored in inventory for potential use in the procedure. In the example, the weighted scores 320 may represent fractional quantities to indicate that there is a relatively low likelihood that the item will be used. For example, a probability of use that is less than 15% may be assigned a weighted score of "0.3," representing roughly one third of the item. This indicates, for example, that one item should be stored for every three scheduled procedures having this likelihood of use. A probability between 15% and 30% may be mapped to a weighted score of "0.6." A probability of greater than 30% may be assigned a weighted score of "1," representing a full implant should be stocked to meet the potential need for the procedure. Other mappings or weightings of probability values may be used.

In some instances, weighted scores 320 for different procedures may be added together or otherwise combined to determine predicted quantities of items needed for a set of multiple procedures. The weighted scores for different patients receiving the same type of procedure may be added together, to determine an estimate of needs for that procedure type. For example, the weighted scores may be added together for patients who each are scheduled to have a total knee replacement, or for patients who are each scheduled to have a cruciate-retaining total knee replacement for the left knee. In addition, or as an alternative, the weighted scores for different patients receiving different types of procedures may be aggregated. For example, weighted scores for scheduled knee replacement, hip replacement, and other joint replacement procedures may be added to determine an overall predicted need across all joint replacement procedures.

In some implementations, surgeon preferences may be used to adjust the probability measures, such as the outputs 310a-310f of the predictive model 112 or the weighted scores 320. The surgeon preferences may be explicitly indicated by the surgeon or may be inferred from a history of procedures performed by the surgeon. For example, if a surgeon historically chooses a larger size than is typical for a certain range of patient heights or other patient characteristics, the probability measures may be adjusted to shift the probability distribution toward larger sizes by an amount that reflects the surgeon's typical practice. As another example, if a surgeon typically uses posterior stabilized implants in a majority of knee surgeries, the probabilities for use of cruciate-retaining implants may be decreased and the probabilities for posterior stabilized implants may be increased.

In some implementations, the predictive models 112 also indicate backup components that may be needed. For example, although a surgeon may prefer to use cruciate-retaining implants for procedures, there is a likelihood that during surgery conditions may require the surgeon to use a posterior-stabilized implant as a backup. The predictive models 112 may indicate the likelihoods of needing the alternative or backup items, both according to the surgeon's historical use of the backup options and according to safety rules that provide at least a minimum number of backup options to be provided generally to limit risks to patients.

Figure 3B:
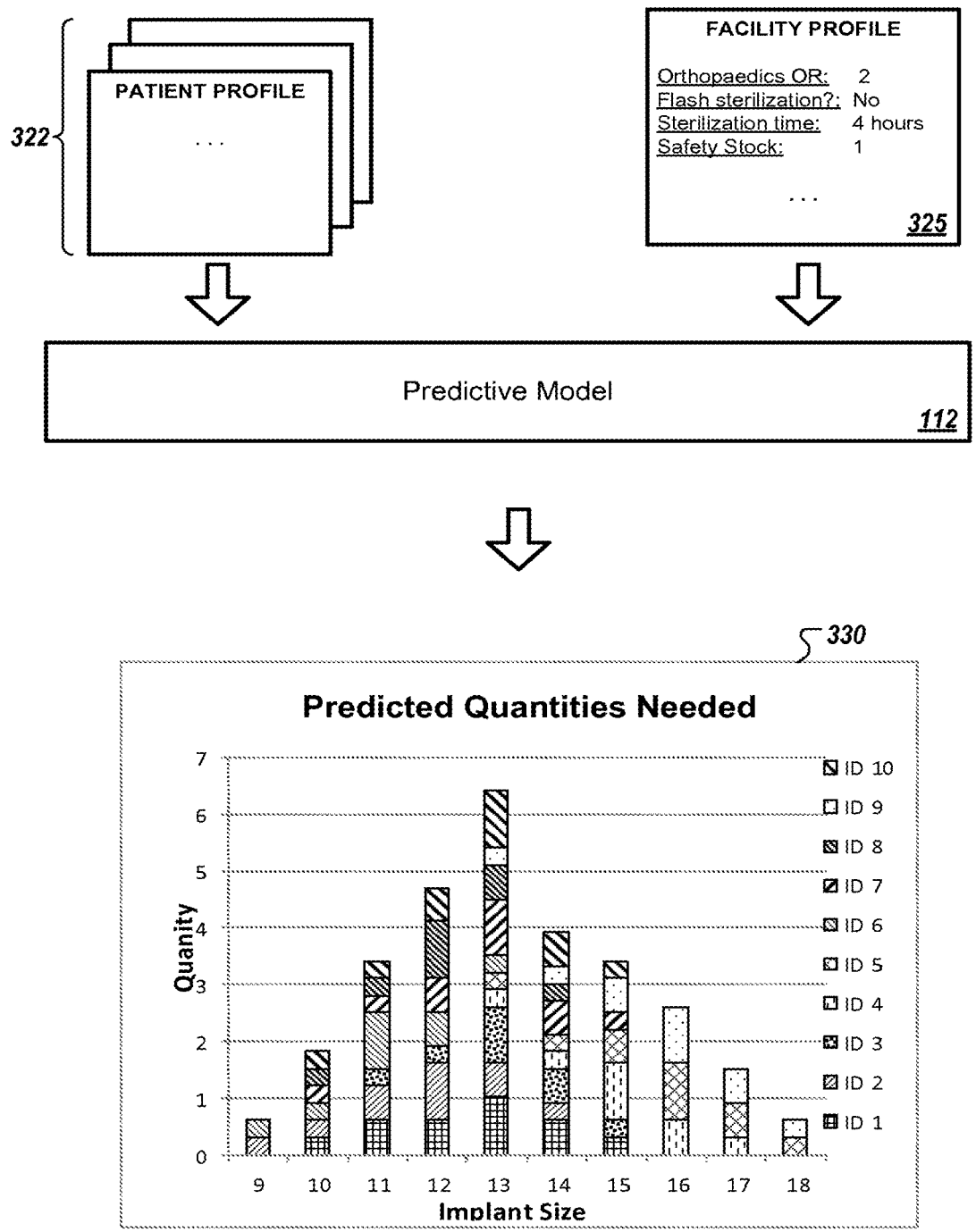

Referring to FIG. 3B, the probability values for multiple procedures can be combined to predict an inventory level needed to satisfy the likely needs of a medical facility. For example, a set of scheduled procedures is selected, for example, all knee replacement procedures scheduled for the next month. A set of patient profiles 322, which includes patient data for each of the knee replacement procedures, is accessed. Each of the patient profiles 322 may include some or all of the types of information discussed for the patient profile 302 of FIG. 3A. These patient profiles 322 are input to the predictive model 112, resulting in a set of scores, such as the outputs 310a-310f or the weighted scores 320 of FIG. 3A, for each of the individual procedures. Other information, such as physician profiles and procedure profiles associated with each patient profile 322 may be provided and used in the same manner as shown in FIG. 3A.

The predictive model 112 may be configured to aggregate the potential needs indicated by the probability distributions for the different patients. One manner in which the predictive model 112 may aggregate the likelihoods that different items will be used is to generate weighted scores corresponding to each patient profile, and then add the sets of weighted scores together.

In some implementations, a facility profile 325 is also input to the predictive model 112, to indicate characteristics and preferences of the medical facility where the procedures are scheduled to be performed. For example, the facility profile 325 may indicate how many operating rooms are assigned for different type of procedures, whether flash sterilization is allowed, how much time is required for sterilization between uses of implants, and a safety stock level or minimum inventory level to be maintained. Using this information, the predictive model 112 may predict the quantity of instruments, trial components, and other supplies that are likely to be needed.

The output of the predictive model 112 may indicate predicted quantities of items that should be stocked to meet the needs predicted for the selected procedures. In the example of FIG. 3B, the predictive model 112 determines quantities of implants needed to complete a set of procedures for ten different patients, referred to as ID1 thorough ID10. The output of the predicted model 112 is shown as a chart 330, which shows quantities needed for various implant sizes. For purposes of illustration, the chart 330 shows how the probability distributions or weighted scores for the ten different patients contribute to the overall inventory need of the medical facility. The quantity estimate provided for each implant size may be rounded, for example, to the nearest integer or rounded up to the next integer, and used as a desired quantity to stock each of the implant sizes. The aggregation of probability distributions for multiple procedures can increase the accuracy of predictions of inventory needs for the medical facility overall.

In some implementations, the predictive model may be customized or tailored for a specific institution, medical facility, demographic, or region. For example, one or more predictive models 112 may be initially generated using data for a general population. The models 112 may then be customized through further training or refinement with examples specific to a target population. For example, adjusting the models 112 using historical data for a specific medical facility may produce a new model that is more accurate at predicting the needs of patients at that specific medical facility. Similarly, adjusting the parameters of a model using historical data for patients in a specific region may allow a model to represent the particular characteristics of the population of that region. The models 112 may be customized for, for example, a particular continent, country, state, city, zip code, or other geographic area. Further, the decision whether to generate or use a customized model may be determined by analysis of predictions made by one model relative to the actual outcomes observed, e.g., the implant components actually used. When variation between predicted and observed outcomes exceeds a threshold amount, for example, when differences reach a threshold level for at least a minimum period of time, the need for a more accurate, customized model may be determined.

In some implementations, the outputs of a predictive model or other probability measures may be influenced by probability measures for other components. Frequently, a prosthesis such as an artificial knee involves several components that are assembled during surgery. When implant components are to be used together, typically only a limited range of sizes of one component are compatible with other sizes of components. For example, a femoral component of an artificial knee may be compatible only with a tibial component of the same size, or with a tibial component of plus or minus one size of the femoral component. By training of the predictive models 112 with historical data about actual procedures that have been performed, some or all of these dependencies may be reflected in the probabilities generated by the models 112. In some implementations, the probabilities generated by one model 112 may be used as input to another model 112 to improve accuracy. For example, the output of a first model 112 for a femoral component may be provided as input to a second model 112 for a tibial component, allowing the second model 112 to more accurately assess the likelihood of different sizes in view of the range of likely femoral component sizes. In addition, or as an alternative, a set of rules may be applied to weight or otherwise adjust probability distributions for different implant components so that implant component size predictions reflect sizes that are compatible with each other.

Figures 3C, 3D:
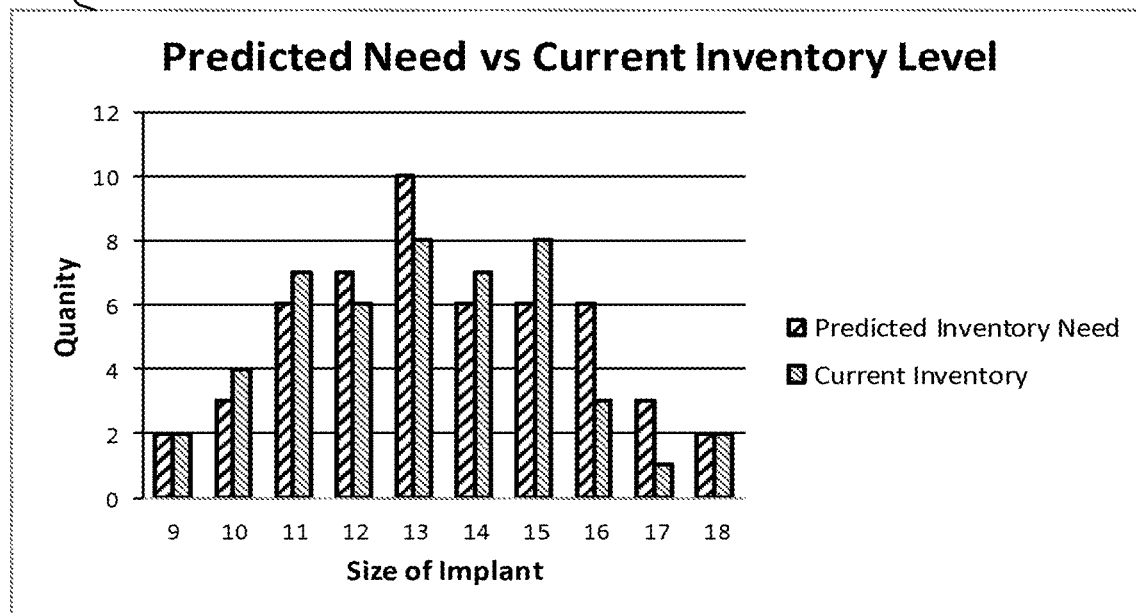

Referring to FIGS. 3C and 3D, predicted needs of a medical facility may be compared with actual inventory levels at the medical facility to determine inventory adjustments. The data shown in FIGS. 3C and 3D may be generated by the scheduler 110, and may be used by the scheduler 110 to determine how inventory levels should be adjusted. The data can also be provided to users in various forms, as discussed below with respect to FIG. 4. FIG. 3C is a chart that shows predicted quantities of implants needed for a set of scheduled procedures and the corresponding quantities of implants actually in the inventory of the medical facility. FIG. 3D is a table 342 that shows, for various implant sizes 344, a safety stock level 345, a predicted need 346, a current inventory level 347. The table 342 also indicates differences 348 between the predicted needs 346 and the current inventory levels 347. In some instances the predicted need 346 represents quantities of items needed to ensure that there is at least a minimum confidence level that each of different sizes of implant components will be available at the particular medical facility. These quantities can be the smallest quantities that provide the minimum confidence level, or quantities that provide the minimum confidence level with no more than a maximum excess amount.

The safety stock levels 345 indicate minimum quantities that should be stocked at all times, even if no upcoming use is predicted. For example, some medical facilities may prefer to always have at least one unit of each of the various implant components in inventory to limit the risk that a needed component will be unavailable. Even if the predicted need 346 for an implant size is less than the corresponding safety stock level 345, then the inventory at the medical facility should include at least this minimum, safety stock level. In some instances, the predicted need 346 is set using the safety stock level 345, so that the level of predicted need 346 is always indicated to be at or above the safety stock level 345. In some instances, the scheduler 110 or the medical facility may determine that the predicted need should include the safety stock level 345 plus the amount of items that the scheduler 110 predicts should be available to meet the likely needs of patients.

As shown in FIG. 3D, the differences 348 indicate that there are several implant sizes where the current inventory is less than predicted need. The scheduler 110 may take various actions to adjust inventory at the medical facility to address the differences 348. For example, the scheduler 110 may send an alert to a user, such as a hospital employee, to indicate the shortfall. In some implementations, the scheduler 110 may automatically generate an order to purchase the needed items or otherwise have the needed items delivered to the medical facility.

Figure 3E:
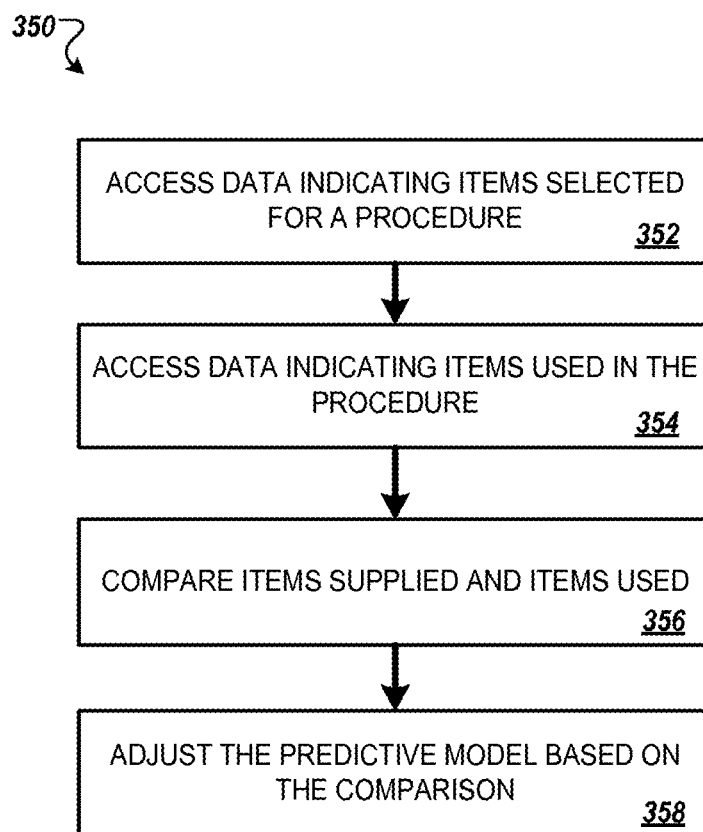
FIG. 3E is a flow diagram indicating an example of a process for adjusting a predictive model.

Referring to FIG. 3E, a process 350 may be used to update the predictive model 112. After the predictive model 112 is used to generate predictions of items needed for a medical procedure, information about which items are actually used can be tracked and used to increase the accuracy of the predictive model 112. The process 350 may be performed by the scheduler 110 or another computing system.

In step 352, the scheduler 110 accesses data indicating a set of items designated to be provided for a medical procedure. For example, the items that the scheduler 110 selected for the procedure may be accessed from an electronic medical record (EMR) database associated with a case ID for the medical procedure.

In step 354, the scheduler 110 accesses data indicating items that were actually used during the medical procedure. For example, records of the medical procedure may indicate that one implant component was opened and implanted, and that another implant remained unopened and was returned to inventory after the medical procedure. During surgery, a bar code reader, RFID scanner, or other scanner may record the tracking code for items that are used, and associate the scan with an event and location, such as opening the package in the operating room.

In step 356, the scheduler 110 compares the set of items provided with the set of items used. The scheduler determines whether there are any differences between the two sets, for example, if one or more items provided were not used, or if one or more items were used that were not reserved ahead of time and designated for the medical procedure.

In step 358, if there are differences between the set of items provided and the set of items used, the scheduler 110 adjusts the predictive model. The predictive model 112 may be, for example, a set of rules learned through regression analysis. Accordingly, records of the patient characteristics and other input that was input to the predictive model, as well as the items actually used in the procedure, may be added to a data set used to generate the rules of the model. Regression analysis may be performed again using the modified data set, to reflect the additional information gained as a result of performing the procedure.

As another example, the predictive model 112 may be a machine learning classifier, an artificial neural network, a support vector machine, a kernel machine or other machine learning model. Parameters of the model may be adjusted by using the information about the completed medical procedure as an additional training example. The adjustment may be achieved by inputting the patient profile and other model inputs, and determining target output values, such as a set of likelihood values that correspond to a revised distribution, that reflect the information about the items actually used in the medical procedure. The predictive model 112 may be adjusted until the predictive model 112 produces outputs that are within a predetermined tolerance of the target output values.

For example, the predictive model 112 may be adjusted so that, for a first component that was provided but not actually used in the medical procedure, the adjusted predictive model 112 indicates a lower likelihood for the first component than the unmodified model, when the adjusted and unmodified models receive the same inputs. Similarly, the predictive model 112 may be adjusted so that, for a second component that was not provided but was actually used in the medical procedure, the adjusted model indicates a higher likelihood that the second component will be used, relative to the output of the model prior to adjustment.

As an example, a surgeon may perform 30 knee replacement surgeries a year on females under 5'6". The initial output of the predictive model 112 may have indicated that a posterior-stabilized femoral component of size 2, size 3, and size 4 should each be provided for females under 5'6". However, the records of the actual surgeries may indicate a size 2 femoral component was used in 26 of the 30 surgeries, and that a size 4 femoral component was not used in any of the 30 surgeries. After updating the predictive model 112 based on this distribution of observed component usage for patients that are females under 5'6", the predictive model 112 will indicate a reduced likelihood of size 4 components being needed for that class of patient. Thus, for future surgeries for females under 5'6", the predictive model 112 may indicate that only the size 2 and size 3 femoral components are needed, so that the size 4 will not be supplied to the operating room.

In some implementations, the scheduler 110 applies weights to training data to control the effect that the data has on the predictive model 112 during training. Training data that is generated at a location geographically near the medical facility where the medical procedure was performed can be given more weight than data for procedures performed farther away. Similarly, when training a model that takes into account preferences of a particular surgeon, a higher weight may be given to data about surgeries of the particular surgeon than for surgeries by other surgeons. For example, a model may represent selections of items for a particular surgeon. A base weight of "1" may be assigned for general data. A weight of "2" may be assigned to data about surgeries within the same state as the particular surgeon. A weight of "3" may be assigned to data about surgeries in the same metro area as the particular surgeon. A weight of "4" may be assigned to data about surgeries performed at the same hospital where the particular surgeon operates, and a weight of "5" may be assigned for data about surgeries actually performed by the particular surgeon. In this manner, the model may be trained using a broader base of data than the set of surgeries performed by the particular surgeon, since such a limited data set may be insufficient to effectively train a model. At the same time, the training process places emphasis on the data that is likely to be most relevant, in order to improve accuracy and capture information about the unique preferences of the particular surgeon.

In some implementations, predictive models are updated based on assessing the predictions made over particular time periods. For example, the predicted probability distribution or predicted item quantity distribution for a week, a month, a quarter, or a year may be compared with the actual distribution of items used over the same period. The predictive model may then be updated, based on the differences identified, to produce predictions that more accurately coincide with the actual usage observed.

Figure 4:
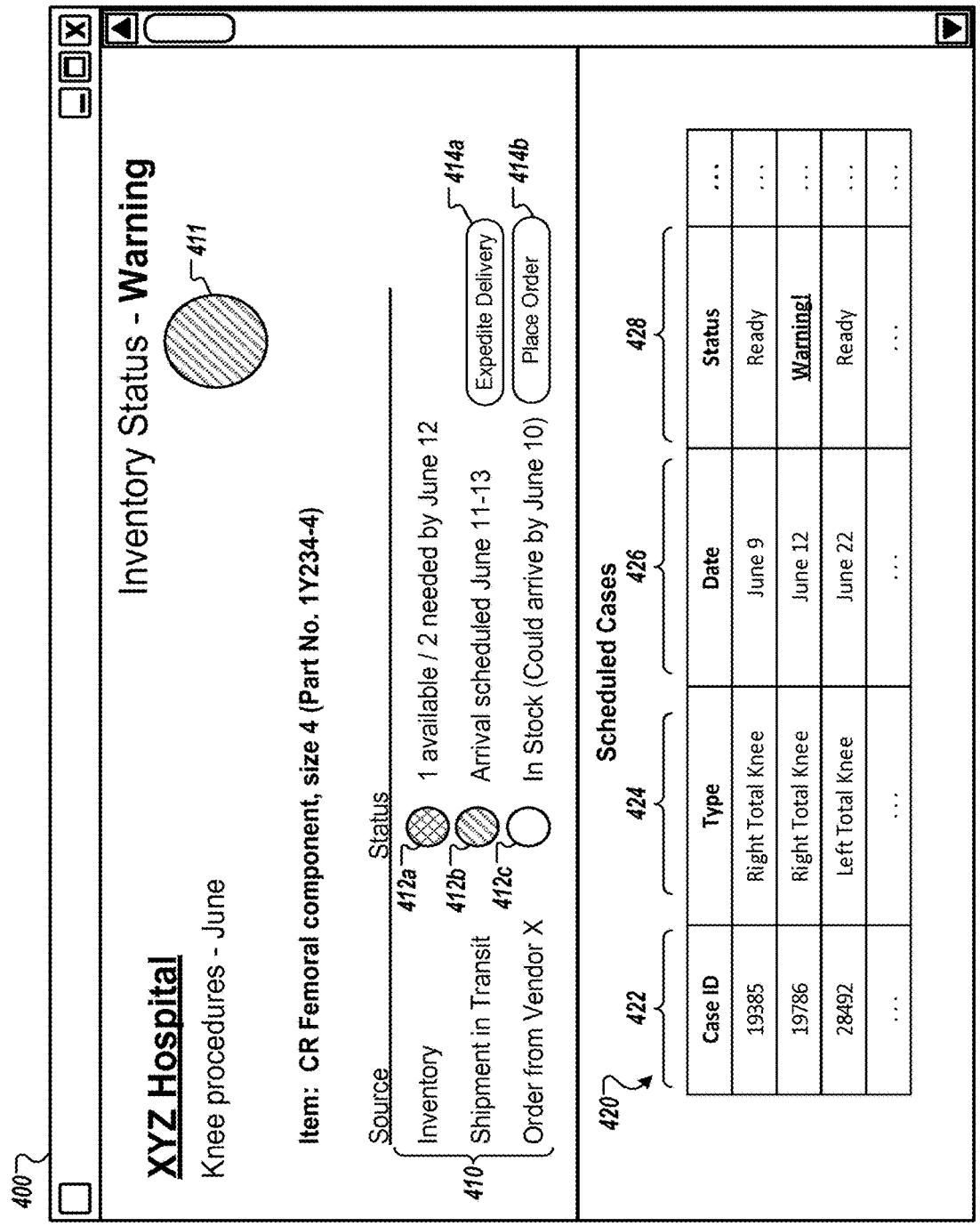
FIG. 4 is a flow diagram that illustrates an example of a process for locating a medical device.

Referring to FIG. 4, if the scheduler 110 determines that a medical facility's inventory does not include items needed for a planned surgery, the scheduler 110 may provide a warning to the medical facility, for example, through the medical facility app 160 or another interface. The warning may indicate, for example, that further action needs to be taken to ensure inventory will be present for one or more procedures. The scheduler 110 can generate measures of predicted inventory needs on a running basis, for example, hourly, daily, weekly, and so on, to maintain an up to date estimate of upcoming needs. The scheduler can provide warnings and updates, or take corrective action to adjust inventory levels, whenever new procedures or other events result in predictions that exceed available inventories.

In the example of FIG. 4, a user interface 400 displays data provided by the scheduler 110 to indicate the status of an item needed for upcoming knee replacement surgeries. In particular, a cruciate-retaining femoral component of size 4, which has a part number of "1Y234-4," is predicted as being likely to be needed for two different surgeries scheduled for the month of June, but only one of the items is available in inventory. A status area 410 of the user interface 410 indicates different sources for the component, and whether the various sources can provide the component before the scheduled date of surgery, June 12.

One or more indicators 411, 412a-412c may be provided to indicate the status of one or more items that are predicted to be needed. The indicator 411 shows the overall status of the inventory for a medical procedure or set of medical procedures. If components indicated as likely to be used are not available, the status indicator 411 can indicate a need for further action. The indicators 412a-412c indicate the availability of items from different sources. The indicators 411, 412a-412c may be colored to represent an availability status. For example, a green indicator may indicate that items have a high likelihood of being available when needed, for example, having a likelihood of at least a minimum threshold such as 90%. A yellow indicator may indicate that items have a lower likelihood of being available, for example, in a range such as between 60% and 90%. A red indicator may indicate an even lower likelihood, such as below 60%.

In the example, the indicator 412a is red, indicating that the local inventory at the hospital does not include a sufficient quantity of the component. The indicator 412b, which corresponds to a shipment in transit, is colored yellow to indicate that the component may arrive, but there is a significant possibility that it may not be available on time. For example, the shipment is scheduled for delivery between June 11-13, but the delivery at the end of the range, potential for delays, and time needed to process the shipment on arrival could result in the component being unavailable at the time of surgery. The indicator 412c is colored green, indicating that a vendor has the needed component in stock and can ship it so that it arrives by the time of surgery.

The user interface 400 includes interactive controls 414a, 414b that permit a user to take action to secure the items needed for the surgery. For example, the user may click or otherwise interact with the control 414a to expedite the shipment in transit to ensure delivery in time for the scheduled June 12 surgery. The user may alternatively use the control 414b to initiate a purchase of the component from a vendor. Once the user indicates the desired action for obtaining the needed component, the scheduler 110 takes the necessary action, for example, by communicating with the shipping company to alter shipping plans, or to transmit a purchase order for the component from a vendor or sales representative. In some implementations, the scheduler 110 takes actions such as initiating purchases only after a user confirms the action is desired. Nevertheless, in some implementations, the scheduler 110 may automatically initiate purchases and arrange deliveries in accordance with previously provided rules or authorization from the medical facility, without requiring human input in advance.

Other information may be provided on the user interface 400 or other user interfaces provided by the scheduler 110. For example, the user interface 400 may indicate prices of the component, or differences in prices, among the various sources. Similarly, the user interface may indicate whether contractual agreements affect the choice of which source to select.

In the example, the user interface 400 shows case information 420, allowing the user to see information about scheduled procedures and whether the scheduled procedures may be affected by inventory issues. The inventory information 420 indicates a case ID values 422 for various procedures, as well as the procedure type 424 and scheduled date 426 for each procedure. The case information 420 also includes status information 428, which can indicate which case(s) may be affected by a projected inventory shortage.

Figure 5:
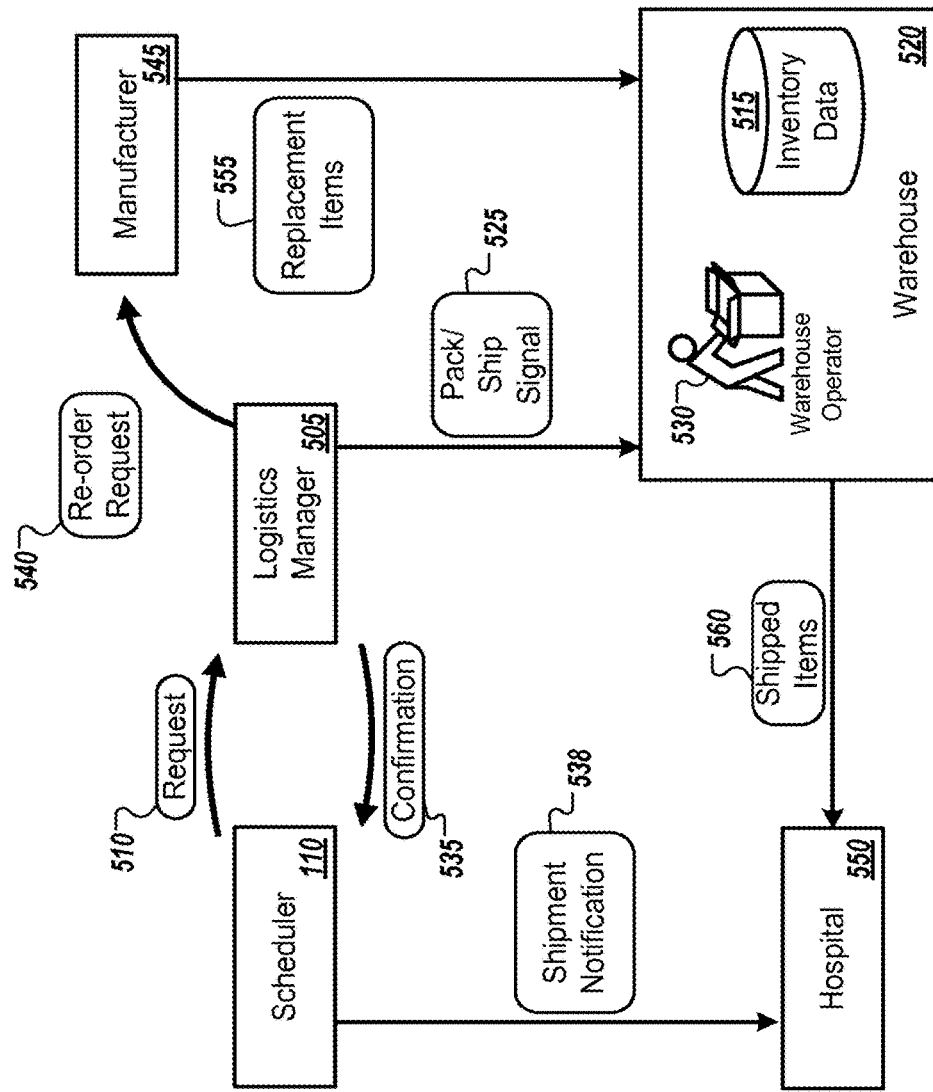
FIG. 5 is a diagram that illustrates an example of a user interface showing inventory information.

Referring to FIG. 5, the scheduler 110 may interact with a logistics manager 505 to obtain items needed for medical procedures. The logistics manager 505 interacts with computer systems at a warehouse 520 and a device manufacturer 545 to arrange for delivery of items to a hospital 550. The logistics manager 505 may be a computer system or computer interface provided by a third party, such as a medical device vendor or manufacturer. The scheduler 110 may communicate with the different parties in the supply chain using plug-in modules to access databases and records managed by different software platforms. In some implementations, one or more of the functions performed by the logistics manager 505 may be performed by the scheduler 110 or software module accessed by the scheduler.

When the scheduler 110 determines that a medical facility's inventory does not include items needed for a planned surgery, the scheduler 110 may send a query or other request 510 to the logistics manager 505 to request that the logistics manager 505 arrange for needed items to be provided. The request 510 indicates, for example, the items needed, the case ID for the procedure, and the date that the items are needed.

In response to the request 510, the logistics manager 505 accesses a warehouse inventory database 515 to determine whether an associated warehouse 520 has available items that match the ones indicated in the query 515. Because some warehouse inventory may already be reserved for other scheduled surgeries, some items physically present in the warehouse 520 may not be available for satisfying the request 510. Similarly, some warehouse inventory may have been shipped from a loaner program or a medical device manufacturer's storage facility and may not yet have arrived at the warehouse 520, and thus may be designated with an "in transit" availability status, along with an indication of a time available stamp.

If there is sufficient warehouse inventory for the surgery, or sufficient projected inventory (e.g., considering items in transit and currently available), the logistics manager 505 causes the needed items to each be tagged with the case ID and deducted from the list of available inventory at the warehouse 520. At this time, or when prompted by an operator, the logistics manager 505 may send a pack/ship signal 525 to the warehouse operator 530. The implant components or other items indicated by the request 510 are gathered, packed and shipped from the warehouse 520 to the hospital 550. The shipped items 560 are then delivered at the hospital 550.

With the shipment process initiated, the logistics provider 505 sends a confirmation 535 to the scheduler 110, indicating which items have been shipped and when the items are scheduled to arrive. This allows the scheduler 110 to send a shipment notification 538 to the hospital 550, which updates the hospital's records to show the items in transit. Even if the warehouse inventory is not immediately shipped, the quantities can be updated to reflect the upcoming need. The case status that the scheduler 110 provides (for example, indicator 411 of FIG. 4) may be updated to show that timely delivery of the items has been secured. For example, a status indicator for the case may be changed from "yellow" to "green" for all users that interact with the scheduler 110.

The logistics manager 505 may also send a re-order request 540 to the manufacturer 545 of the shipped items 560, prompting the manufacturer 545 to send replacement items 555 to the warehouse 520, in order to maintain sufficient inventory at the warehouse 520.

On arrival at the hospital 550, the items are scanned with a bar code reader or other scanning device for tracking purposes. One example of a vendor who could supply the bar code reader and operating room interface is Orthosecure.

If there is not sufficient third party warehouse inventory for the surgery, the scheduler 110 or the logistics manager 505 calculates alternative options to get the required implants to the hospital 550 at the scheduled date. Among the options might include building a rush implant component at the orthopedics company manufacturer, reviewing the status of any implants in transit, expediting the shipment of existing manufacturer inventory, reviewing the inventory at other hospitals around the country for any they might spare, etc. If a needed implant cannot be provided in time for the surgery, the scheduler 110 may alert the hospital 550 that implants from another implant vendor should be considered. A sales representative may also inform the surgeon or a hospital administrator that the implants cannot be secured with a high degree of confidence.

Figure 6A:
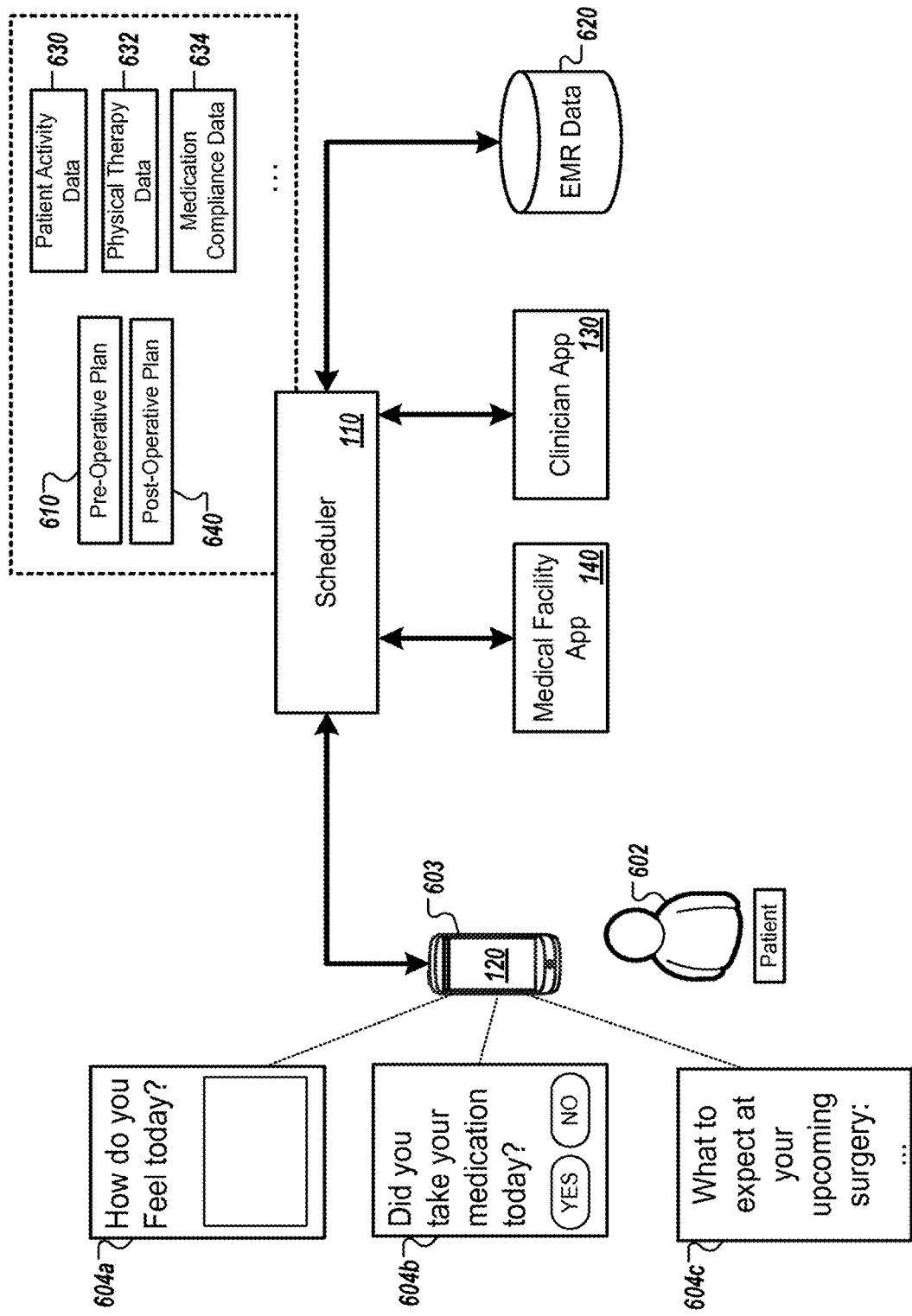
FIG. 6A is a block diagram that illustrates an example of pre-operative and post-operative data collection and patient communication.

Referring to FIG. 6, after a medical procedure is scheduled, the scheduler 110 may interact with a patient 602 to encourage and track compliance with a pre-operative regimen. After the patient's medical procedure has been scheduled by the patient's physician using the scheduler 110, the scheduler 110 communicates with the patient 602 through the patient app 120, which the patient may have downloaded to the patient's tablet computer, smartphone, desktop computer, or other client device 603. Alternatively, the patient 602 may access an equivalent interface through a web page or other interface.

Frequently, patients are prescribed medication and physical therapy in preparation for surgery. Failure to adhere to the prescriptions may increase the risk of unfavorable outcomes or may increase recovery time. In some instances, a patient's failure to comply with a pre-operative regimen may require a surgery to be postponed or cancelled. The scheduler 110 may store the pre-operative plan 610 for the patient 602, which can allow the scheduler 110 to customize communications specifically for the patient 602 based on the plan data. Thus the scheduler 110 can provide accurate reminders and information about actions needed to comply with the pre-operative plan.

The patient app 120, operating independently or in response to directions from the scheduler 110, may help the patient 602 to comply with the pre-operative regimen. For example, the patient app 120 may provide messages 604a-604c, as well as games and other content. The patient app 120 may provide messages that encourage the patient, for example, by praising the patient for compliance or indicating the benefits of compliance with the pre-operative plan. The messages may remind the patient, for example, with messages such as "did you stretch today?" or "it's time to take your medicine." Other messages, such as message 604c, inform the patient and help the patient 602 set realistic expectations for the upcoming procedure.

The messages and other content provided by the patient app 120 can be used to gather data from and about the patient 602. For example, the message 604a asks the patient how she feels and includes an area for the patient to input a response. As another example, the message 604b asks the patient 602 whether she has taken her medicine. The patient's responses can be stored as medication compliance data 634. Questionnaires, games, and other interactive content may additionally be used to prompt patients to provide information. In this manner, the patient app 120 may obtain information indicating whether the patent is complying with specific aspects of the pre-operative plan.

The input that the patient 602 provides is transmitted over a network to the scheduler 110, which stores and processes the information. The scheduler 110 may maintain a history of any or all of the patient's interactions with the client app 120 that reflect compliance or lack of compliance. These inputs may be used to select appropriate pre- and post-surgery interventions to assist the patient, for example, when the information satisfies predetermined criteria. For example, when a patient reports consistent or high levels of pain, or the patient exhibits signs of anxiety, the scheduler 110 may alert the clinical team. The scheduler 110 may, in some instances, trigger notifications for the clinical team to take certain recommended actions, such as to call the patient, adjust pain management strategies or physical therapy, and so on.

The scheduler 110 can obtain other data which may be used to assess the wellbeing of the patient 602 and compliance. For example, the patient app 120 may access data from sensors of the patient's client device 603. The patient app 120 may interpret data from the sensors in order to act as a pedometer to record a number of steps taken, or may otherwise record activity of the patient. When the client device 603 is a mobile device, such as a smartphone or other carried device, movement of the client device 603 can reflect at least some movement of the patient 602. This data can be provided to the scheduler 110 and can be stored as patient activity data 630. In addition, the scheduler 110 may receive and store physical therapy data 632 from a physical therapist indicating the patient's progress, whether the patient 602 has attended scheduled sessions, and so on. Data obtained by the patient app 120 and/or scheduler 110 may be stored in electronic medical records (EMR) 620 of the patient's physician and/or the medical facility where the medical procedure will be performed.

The information that the patient app 120 and the scheduler 110 obtain can be used to determine whether surgery is on track to proceed. If necessary, the scheduler 110 may re-schedule or cancel the patient's surgery, for example, when a predetermined level of non-compliance has occurred, or when directed by the physician.

After a patient's surgery, the patient app 120 may continue to communicate with the patient 602. The scheduler 110 stores a post-operative plan 640, and monitors the patient's compliance with the post-operative plan 640 in the same manner that it monitors the pre-operative plan 610. For example, the scheduler 110 may provide information to be displayed at the patient app 120 that indicates what is typical of recovery from the procedure, and remind the patient of actions needed to follow the post-operative plan. The patient app 120 may also indicate which activities the patient 602 to should avoid in order to allow proper recovery.

The data can also be used to help build a patient's confidence by showing that the patient is improving from day to day, and showing how the surgery has provided an improvement in the patient's quality of life. The patient app 120 may provide information that demonstrates the patient's progress and improvement. For example, information can be provided that shows comparisons of pre-operative and post-operative data. The information provided to the patient 602 may indicate, for example, that the amount of pain reported to the app 120 has decreased, or that pedometer data shows more activity after surgery than before surgery. When appropriate, the data for the patient 602 may be compared with data about other patients, for example, to reassure the patient that recovery is in line with expected or average measures, or that the patient is recovering at an above-average rate. In some instances, a physician's reimbursement or payment rates may be tied, at least in part, to a patient's subjective satisfaction. By reminding the patient 602 of positive outcomes of the surgery and post-operative recovery phase, the patient 602 may be more inclined to hold a favorable view of the surgery and its outcomes.

Figure 6B:
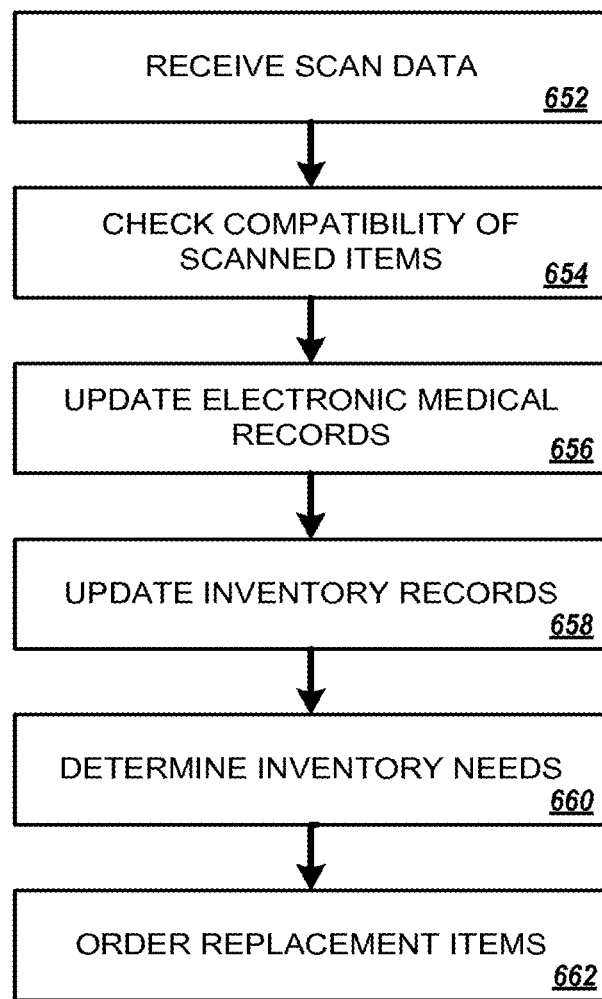
FIG. 6B is a flow diagram that illustrates an example of a process for providing and tracking implants.

Referring to FIG. 6B, the scheduler 110 may perform a process 650 to manage inventory during and after a medical procedure. For example, the scheduler 110 may receive data that identifies items being used in a medical procedure, and then may check compatibility, update records, and re-order items as needed. The scheduler 110 may dynamically interact with suppliers, manufacturers, and others as items are used in order to automatically replenish inventory at a medical facility.

At step 652, the scheduler 110 receives data indicating items to be used in a particular medical procedure. During a medical procedure, a physician or other staff member may scan a code associated with an item. The code may be scanned shortly before use, for example, just before sterile packaging for the item is opened in the operating room. The codes or other identifiers generated by the scans may be transmitted to the scheduler 110, along with the case ID for the procedure. The scans may indicate the type of item used, for example, with a product code or SKU, and/or may indicate more specific information about the item, such as a unique serial number or production lot number.

At step 654, the scheduler 110 checks the compatibility of the scanned items. For example, the scheduler 110 may check the items against the surgical plan associated with the case ID to determine if there are any discrepancies. As a result, the scheduler 110 may warn the operating room staff if, for example, the surgical plan for a patient indicates a left knee replacement is to be performed, but a component for a right knee prosthesis is scanned. The scheduler 110 also checks the scanned items for compatibility with each other. For example, the scheduler 110 determines whether a set of multiple scanned components may properly be used together based on the manufacturer's guidelines or design specifications, government-approved uses, surgeon or hospital policies, or other rules. Thus, if components from incompatible product lines were scanned, or if there is a size mismatch between components that is outside the manufacturer's recommendations, the scheduler 110 warns the operating room staff of the incompatibility. Similarly, the scheduler 110 determines whether any of the scanned items have expired or are subject to recalls, and provides warnings if the scanned items should not be used.

Once the final set of items to be used in the medical procedure have each been scanned, the scheduler 110 updates the electronic medical records for the patient and the procedure to indicate which items are used (step 656). The scheduler 110 also updates the inventory records of the hospital to indicate that the items used in the procedure are no longer available (step 658).

At step 660, the scheduler 110 determines whether additional inventory should be purchased to replace the items used. For example, the scheduler 110 may assess the likely needs of the medical facility as discussed above with respect to FIGS. 2-4 to determine a predicted need for items used, and whether the current inventory is sufficient to meet the predicted need.

At step 662, the scheduler 110 may order items that are needed to meet the predicted needs of the medical facility. As discussed above, the scheduler 110 may access data indicating contractual agreements, reimbursement rates, and price lists to determine an appropriate price for purchasing the items. As discussed above, in some instances the orders may be initiated in response to scans of items or receiving other data from the operating staff that indicates that an item is used in a procedure.

In some implementations, as items are used in medical procedures, the scheduler 110 takes actions to adjust the medical facility's inventory, for example, by sending orders to replenish the used items. The scheduler 110 may communicate directly and automatically with suppliers to cause items to be ordered when the scheduler 110 detects use of the items or another decrease in inventory. In some implementations, the scheduler 110 may generate orders and provide them to human users to review and approve before the orders are sent. The scheduler 110 may be configured to generate and send orders for replacement items within, for example, a week, a day, an hour, a minute, a second or less of receiving data that an item has been used. As a result, the scheduler 110 may cause a desired inventory level to be maintained with real-time or near real-time responses to the scans indicating that items have been used. In some instances, when an item is used in a medical procedure, the scheduler 110 may assess inventory levels and initiate an order for a replacement item before the procedure is completed or soon afterward to quickly bring inventory to the desired level. Thus inventory management operations to address the use of certain items in a procedure can occur concurrently with or begin during the procedure where the items are being used. Alternatively, the scheduler 110 may periodically assess data regarding medical procedures, for example, reviewing records of procedures performed during the previous hour, day, or week, to generate orders to replace items used during a certain period.

Figure 7:
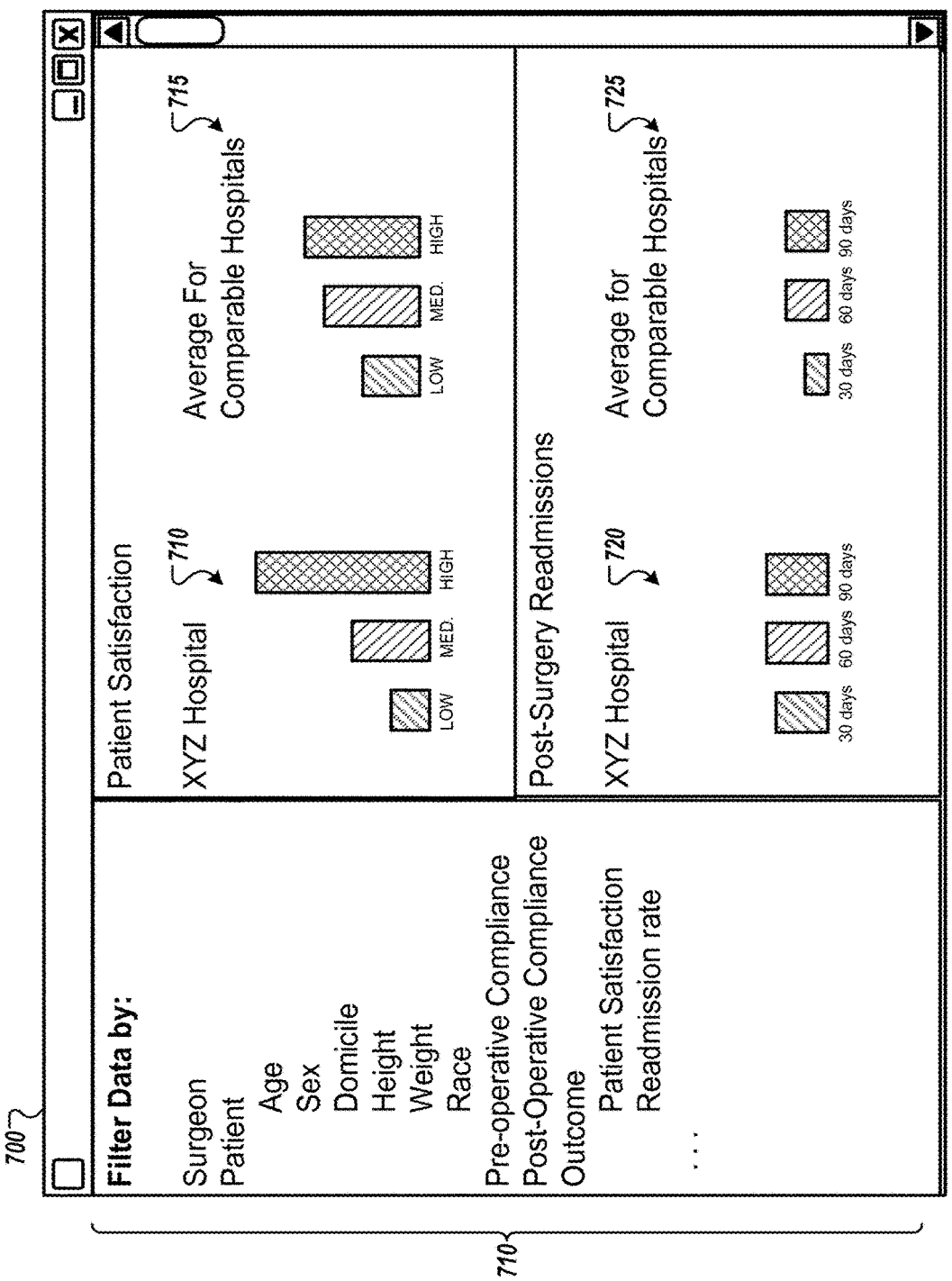
FIG. 7 is a diagram that illustrates an example of a user interface for assessing medical outcomes.

Referring to FIG. 7, a user interface 700 allows a user, such as a hospital, surgeon, or other user, to analyze data about medical procedures and their outcomes. The data provided through the user interface 700 may be provided by an analysis system, which may be the scheduler 110 or another computing system. The information provided may assist users to improve the quality of care provided to ultimately improve patient outcomes and efficiency of future medical procedures.

The user interface 700 provides access to an analytics system, which can allow a hospital to track where inefficiencies are taking place. For example, the readmission of a patient after the patient is discharged can be costly. Some insurance plans only reimburse physicians for one post-operative consultation, so multiple visits may be undesirable. Readmission can occur due to any of a host of factors, including infection, pain, comorbidities, low patient satisfaction, a patient's failure to take medication or to perform physical therapy, etc. Many records of readmissions alone may not reveal the factors that contributed to the conditions requiring readmission. However, the user interface 700 may generate information that indicates correlations between surgical techniques and patient actions and outcomes, allowing users to identify which actions lead to positive outcomes and which actions lead to negative outcomes.

The analytics system accesses a set of underlying data about patients, their medical procedures, and the outcomes of the procedures. For a physician, the analytics system can access information about patients the physician has treated. For a hospital administrator, the analytics system can access information for patients treated at the administrator's hospital. Information about other patients may also be accessed. In general the data accessed through the user interface 700 includes data about patient compliance with pre- and post-operative regimens, which may be collected as discussed above with respect to FIG. 6. The data can also include records of surgical events, such as blood loss volume, whether a tourniquet was used, and so on. The data can also include other data that the scheduler 110 has access to, such as patient profiles, surgeon profiles, hospital profiles, and demographic information.

The user interface 700 permits a user to filter a data set according to various criteria. For example, the user interface 700 includes filter controls 710 that allow a user to select a subset of data according to patient characteristics, surgeon characteristics, compliance characteristics, medical outcomes, and other factors. In response to user input, the analytics system selects a subset of data according to the parameters indicated in the user input. For example, a physician may select a data set representing data for patients treated by the physician who were over age 60. As another example, a hospital administrator may select a data set representing surgeries performed by one of a specific set of surgeons, or a data set representing procedures resulting in favorable patient satisfaction ratings.

Using a user-selected data set or a default data set, the analytics system generates one or more aggregate measures for the data set. For example, the analytics system can determine average outcomes for a set of patients. As another example, when a data set is selected or filtered according to outcome, the analytics system can determine average characteristics of the patients, surgeons, medical facilities, and pre- and post-operative regimens associated with the selected outcomes. The analytics system then provides the calculated measures for display. In the example of FIG. 7, the analytics system provides patient satisfaction levels 710 and readmission rates 720 for the patients of a medical facility, "XYZ Hospital." In some implementations, the user interface 700 may provide controls that permit a user to select which measures or metrics to calculate and display.

The analytics system also selects comparison data, generates measures based on the comparison data, and provides the measures for display on the user interface 700. The comparison data may be data about patients treated by competing surgeons or hospitals, or data about patients treated in particular geographical regions. For example, the comparison data selected for a particular surgeon may be data associated with other surgeons that perform the same procedures as the particular surgeon, or that have patients with similar characteristics as those treated by the particular surgeon. As another example, the comparison data selected for a particular medical facility may be data about patients treated at other medical facilities, where the other medical facilities, for example, are located in nearby geographical areas, treat a patients having similar characteristics to those treated at the particular medical facility, or have a similar sized staff or yearly volume of procedures as the particular medical facility. In the example of FIG. 7, the analytics system provides patient satisfaction levels 715 and readmission rates 720 that represent the aggregated outcomes at a selected set of medical facilities. This allows the user to compare performance of the "XYZ Hospital" with aggregate information about other hospitals.

In some implementations, the comparison data may be data from clinical studies. For example, data from various clinical studies may be made available to allow users to track compliance with regulatory requirements. The analytics system may have an interface that allows access to a clinical studies database, or the analytics system may store copies of clinical study data.

In addition, the tracking data and electronic medical records maintained by the scheduler 110 and other systems may be used to populate various registries. For example, the data could be used to populate hospital-based, regional, or national registries of implants and medical devices. The data may be used to track survivorship, how long implants are used, and other characteristics. Automating the collection of this data may greatly reduce the time, cost, and transcription errors that may result from data entry by hospital staff.

The user interface 700 may also allow other data to be displayed. For example, the user interface 700 may display current data about patients of a surgeon or medical facility, along with historical values or averages. Comparisons to prior data can indicate trends. Similarly, the user interface 700 may allow the user to view information about subsets of the patients associated with a surgeon or medical facility. For example, different subsets of the patients may include a top outcome group, a low outcome group, and a subset of patients having certain patient characteristics in common.

The user interface 700 may provide controls that permit a user to select which comparison data to display. For example, a user may select a set of patients in the same or similar geographic area, a set of patients in an expanded geographic area, a set of patients from hospitals having certain characteristics, an entire set of patients associated with the user, and so on. The user may filter the comparison data set using filter controls or other techniques.

With the user interface 700, the user can access the analysis system to identify unfavorable trends and causes of bad outcomes. Similarly the user can use the information provided to identify causes of good outcomes. The system permits a user to determine why one doctor has better or poorer results than another. As an example, the patients of a particular surgeon may have above average readmission rates. The output of the analytics system may indicate that the patients have unusually high comorbidities and consequent complications. Since the presence of more than two comorbidities often increases a patient's likelihood of readmission, it may be determined that the re-admission rate is due, in significant part, to the comorbidities of the patients treated. In fact, comparison with data for other surgeons who treat patients with similar amounts of comorbidities may reveal that the surgeon's readmission rate is actually lower than average for these types of patients, suggesting that the care provided by the surgeon is especially effective at treating these patients.

In some implementations, the analytics system can determine correlations that exist between outcomes of surgical procedures and data accessed by the analytics system, including patient characteristics, surgeon characteristics, medical facility characteristics, pre- and post-operative patient compliance, surgical events, and more. Thus, the analytics system may determine, for example, which characteristics increase the risk of negative outcomes, and which characteristics are associated with positive outcomes.

In some implementations, the analytics system may review data for the patients of multiple surgeons and hospitals to identify which surgeons or hospitals produce the best outcomes. For example, the analytics system may compare the data of different providers to identify, for example, the lowest readmission rates, highest average patient satisfaction, lowest infection rates, and so on. Once a set of high-performing surgeons or hospitals is identified, the analytics system may compare the treatment patterns of this set and the treatments provided by others to identify differences that account for the differences in outcomes with statistical significance. Similarly, the analytics system may compare treatment histories for high-performing surgeons and hospitals with treatment histories for the other high-performing surgeons and hospitals to identify commonalities in the data that may indicate the factors contributing to the positive outcomes. The analytics system may then recommend best practices, such as pre- or post-operative regimens or particular surgical techniques that other surgeons and hospitals can implement to improve their outcomes.

As another example, by comparing patient data and metrics for different surgeons and hospitals, the analytics system may identify actions that have little or no effect on outcomes, demonstrating that these actions could potentially be eliminated to reduce cost or that an action should be modified to improve effectiveness. Similarly, the comparison of data may be used to identify low-performing surgeons and hospitals, and the characteristics of the care provided, so that the techniques resulting in poor outcomes can be identified and avoided.

Figure 8:
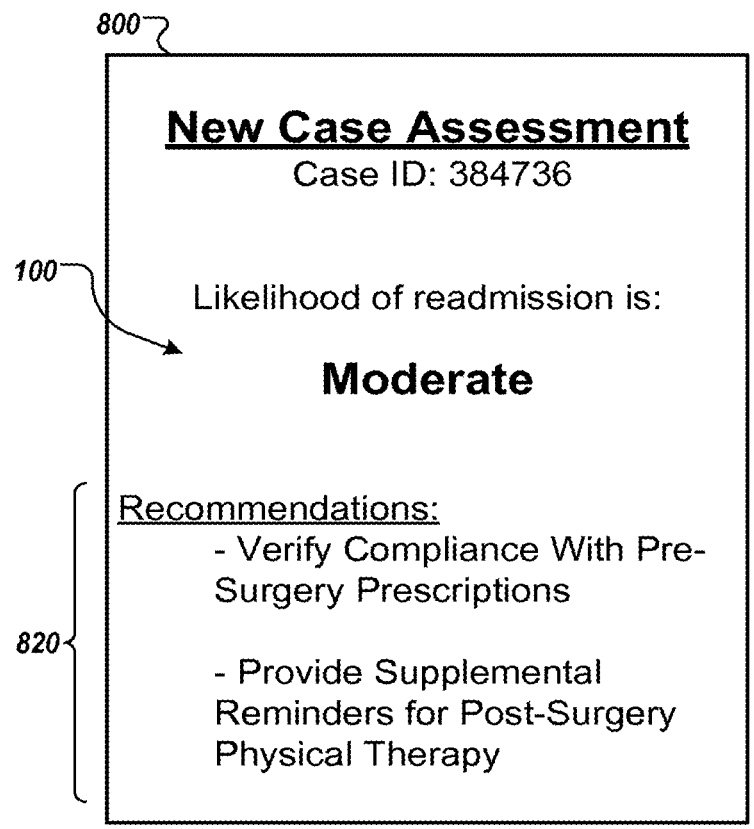
FIG. 8 is a diagram that illustrates an example of a user interface for indicating an assessment of a patient.

Referring to FIG. 8, a user interface 800 shows information provided to a clinician as an assessment of a patient. The information in the user interface 800 may be generated by the scheduler 110 and provided over a network for display at the clinician app 130. In some implementations, data collected about various patients, their pre- and post-operative compliance, and the resulting outcomes of their medical procedures can be used to predict risks and future outcomes for other patients. When a clinician uses the scheduler 110 to schedule a new procedure, information about the patient may be input into a predictive model 112 that is configured to predict characteristics of the outcome of the procedure. For example, the predictive model 112 may provide output that indicates a likelihood of readmission of the patient, or that includes a prediction of the patient's likely level of satisfaction. The predictive model 112 may be used to generate a prediction at any time, for example, before or after the medical procedure.

The predictive model 112 that predicts patient outcomes may be trained using any of the data described above, allowing the model to detect relationships that may exist between outcomes and, for example, patient physical characteristics, surgeon preferences or procedure histories, the medical facility where the procedure is scheduled to be performed, the level of pre- and/or post-operative compliance of the patient, and so on. The data collected about many individual patients may be used as examples demonstrating how each of various factors impacts outcomes.

To generate a prediction, a patient profile, surgeon profile, medical procedure profile, pre- and/or post-operative compliance profile, or other data for the patient is input to the predictive model 112. In response, the predictive model 112 provides scores that indicate likelihoods or scores for the outcome of the patient's procedure. Information about the predicted outcome is then provided on the user interface 800. For example, likelihood scores in predetermined ranges may be mapped to corresponding indicators or classifications. The user interface 800 indicates, for example, that a particular patient has a moderate likelihood of readmission after the medical procedure. The label of a moderate likelihood may represent a likelihood indicated by the predictive model 112 that falls in a range of, for example, 40% to 60%.

The user interface 800 may include recommendations 820 for increasing the likelihood of achieving a positive outcome. The recommendations 820 may be actions that the analytics system has determined to be correlated with favorable outcomes. In particular, at least some of the recommendations 820 may include actions that the analytics system has determined to correspond to above-average results. The recommendations 820 may be selected based on characteristics of the patient. For example, analysis performed by the analytics system discussed above may indicate which treatment protocols or other actions are most strongly correlated with positive outcomes for different groups or classes of patients. The results may suggest, for example, that some interventions are more effective with men than women, or for patients located in one geographical area than another. To provide recommendations 820 for a particular patient, actions are selected that have been determined to correlate with favorable patient outcomes for patients that have, for example, the same or similar age, sex, geographical location, or other characteristics as the particular patient.

Figure 9A:
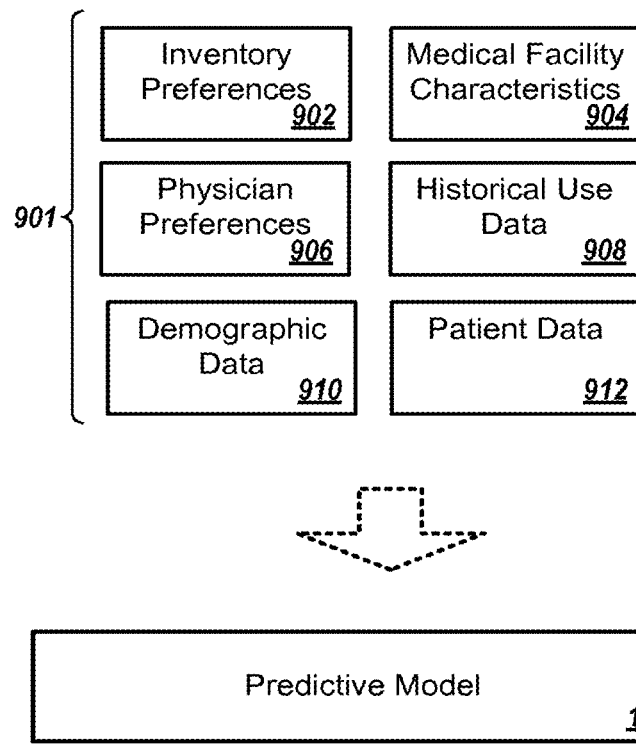
FIG. 9A is a diagram that illustrates an example of generating a predictive model.

Referring to FIG. 9A, a predictive model 112 for surgical inventory modeling can be generated or initialized using a data set 901 that may include, for example, inventory preferences 902 for the medical facility, medical facility characteristics 904, physician preferences 906, historical use data 908, demographic data 910, and patient data 912.

The inventory preferences 902 may include constraints on an amount of inventory that the medical facility would prefer to carry, such as limits to the amount of physical space available to store inventory or limits to the maximum total value of inventory to be carried at a time. The inventory preferences 902 may also include safety stock levels, for example, a minimum number of various items that should be maintained in stock at all times, as a buffer in case an unexpected need arises. For example, one hospital may stock a minimum of one of each implant component, so that there is always at least one component of each different size available. Other inventory preferences 902 may include an indication of how quickly the medical facility would prefer to have items replenished after use.

Each medical facility may have different inventory preferences 902. Some medical facilities are located in major urban areas, where there is access to overnight delivery of items. This may reduce the need for these medical facilities to have inventory on hand. As another example, a medical facility facing greater storage or cost constraints may desire to aggressively manage the level of inventory, and may prefer to store fewer items, even if doing so presents a greater risk of not having, for example, the full range of implants available for a surgery.

The medical facility characteristics 904 include sterilization rules, such as whether flash sterilization is allowed or not, and the amount of time required to sterilize and return items to an operating room. Other medical facility characteristics 904 may indicate the number of operating rooms and their scheduling policies. This information may affect, for example, how many instrument sets are required for the medical facility. For example, if multiple operating rooms are simultaneously scheduled for orthopaedic surgeries, or if a long time is required to sterilize and return instruments, multiple sets of instruments may be required to accommodate the scheduled procedures.

The physician preferences 906 indicate, for example, the preferred types of items for individual surgeons who use the medical facility. One surgeon may prefer to use implants made by a first manufacturer, and another surgeon may prefer to use implants made by a second manufacturer. Similarly, some surgeons may prefer cruciate-retaining knee prostheses, while other surgeons may prefer posterior-stabilized prostheses. Physician preferences 906 may also indicate how many alternative items physicians prefer to have available at the time of a medical procedure. For example, for a knee replacement in which only a single femoral component will be implanted, some surgeons may prefer to have an implant for the estimated size needed as well as implants one size larger and one size smaller. Other surgeons may prefer to have available implants one and two sizes larger and implants one and two sizes smaller, or may prefer to have an implant of every different size available.

The historical use data 908 indicates quantities of items that were previously used at the medical facility. Patterns of use may be indicated for the medical facility as a whole, and/or for surgeons individually. The historical use data 908 may include sales data indicating quantities of items purchased during a prior period.

The demographic data 910 indicates characteristics of the potential patients associated with the geographical area served by the medical facility. In many instances, different implants or other items are needed to treat patients with different demographic characteristics. For example, the femoral offset used for hip replacement implants frequently differs for patients of different races. As another example, the femoral stem sizes used for males are, on average, typically larger in diameter than those implanted into females. Accordingly, information about the demographic makeup of a population residing near a medical facility can help to generate predictions of which sizes of implants will be needed at the medical facility.

As another example, a typical male that receives a knee replacement in a first geographical region may be taller than, and of a different race from, a typical male who has a knee replacement in a second geographical region. As a result, it may be much more efficient for a medical facility in the first geographical region to carry more inventory of larger implants and less inventory of smaller implants. Similarly, a medical facility in the second geographical region would tend to use more small implants than large implants, and would benefit from managing its inventory accordingly.

The patient data 912 indicates characteristics of patients that have had prior procedures performed at the medical facility, for example, information about patients that had surgery in the last year. Certain characteristics, such as a patient's sex, height, weight, age, race, or typical comorbidities may be indicative of the types of implants that are most likely to be needed at the medical facility.

The predictive model 112 may be implemented as a set of rules and may be generated to satisfy the needs of the range of patients the medical facility is expected to admit. The rules may be established manually by a user, or may be generated programmatically by the scheduler 110 based on the data set 901. In some implementations, part of establishing the set of rules includes defining a set of hypothetical patients covering the range of patients the hospital is likely to admit, and setting a default implant to be supplied for each class or group of patients in the set.

In some implementations, the set of rules may be generated by determining, based on the data set 901, different groups that make up the overall population served by the medical facility. Data indicating standard distributions of implants for each group may be accessed. Each distribution may be weighted based on the size of the group relative to the overall population, and the weighted distributions may be added together. Then, the sum of the distributions may be scaled according to, for example, a measure of overall expected demand, such as the number of procedures completed in the prior year.

In addition, or as an alternative, a set of rules may be established through an anthropometric study of preexisting implant and patient data. For example, the data may demonstrate typical implant components and sizes used for patients having certain characteristics. If available, the typical implant selections corresponding to different patient characteristics may be estimated from the patient data 912 for patients that have received treatment at the medical facility. Otherwise, the relationships may be determined from other data, such as data about patients in a local area around the medical facility, data about patients in a nationwide area, or data about another set of patients.

Figure 9B:
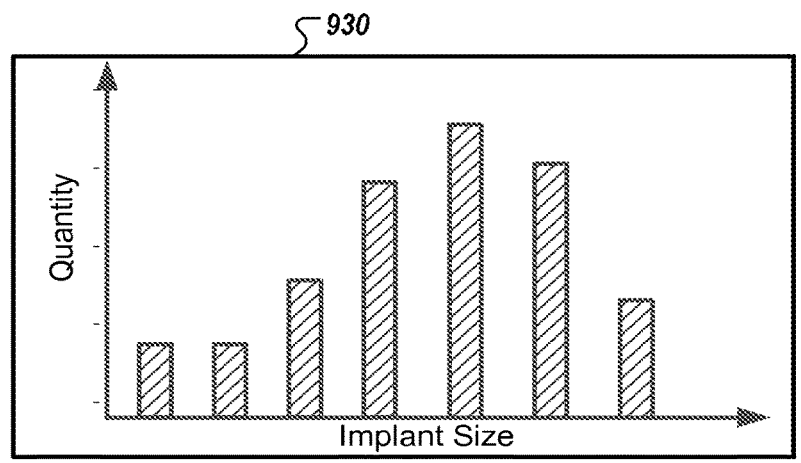
FIG. 9B is a diagram that illustrates an example of a predicted distribution of items.

Referring to FIG. 9B, a predictive model 112 that can predict which items are used for surgeries for individual patients may also be used to determine a predicted distribution 930 of items likely to be used at the medical facility over a period of time, such as a month or a year. This distribution 930 may be used to set an initial level of inventory to stock at the medical facility, or to determine a desired amount of inventory that should be maintained.

In some implementations, the data set 901 is used to determine typical patient profiles corresponding to expected future patients of a surgeon or medical facility. For example, based on demographic information and histories of prior patients, the scheduler 110 may predict that about 60% of knee replacement patients for a particular medical facility are male and 40% are female. The scheduler 110 may determine the breakdown of other characteristics, such as height, weight, and so on, and create a set of hypothetical patient profiles that represent the expected types of patients to be treated at the medical facility. Then each of the expected patient profiles may be input to the predictive model 112 as discussed with respect to FIGS. 2 and 3A to obtain outputs that indicate likely sets of items needed. The various lists of items that predictive model 112 indicates are needed may be added together, to create an aggregate list of items needed for the set of expected patient profiles as a whole. The distribution of items within this aggregate list may be used as the distribution 930 of implants that the medical facility may use as a baseline for setting standard inventory levels to be used at the medical facility over a period of time, such as a month, quarter, or year.

In some implementations, the information about demographics and typical patients are used by a manufacturer to predict which products and quantities should be available for future medical procedures. For example, information about the demographics of a region and/or histories of procedures performed in the region may be used to estimate how many of each size of implant component will be needed for the region. Similarly, the demographic and/or historical information may be used to determine representative patient profiles, which may be provided to a predictive model to determine representative distributions of supplies that should be made available. The predicted needs for the representative patient profiles may be combined to determine an overall prediction of needs for a region. Based on the predicted needs for a region, the manufacturer can adjust the level of inventory that is stocked at a distribution center assigned to meet the needs of that region. In addition, the manufacturer can use predicted quantities needed for multiple medical facilities or multiple geographical regions to set production levels. For example, the manufacturer can adjust the quantities produced for various sizes of implant components to meet an aggregate level of demand predicted.

Figure 9C:
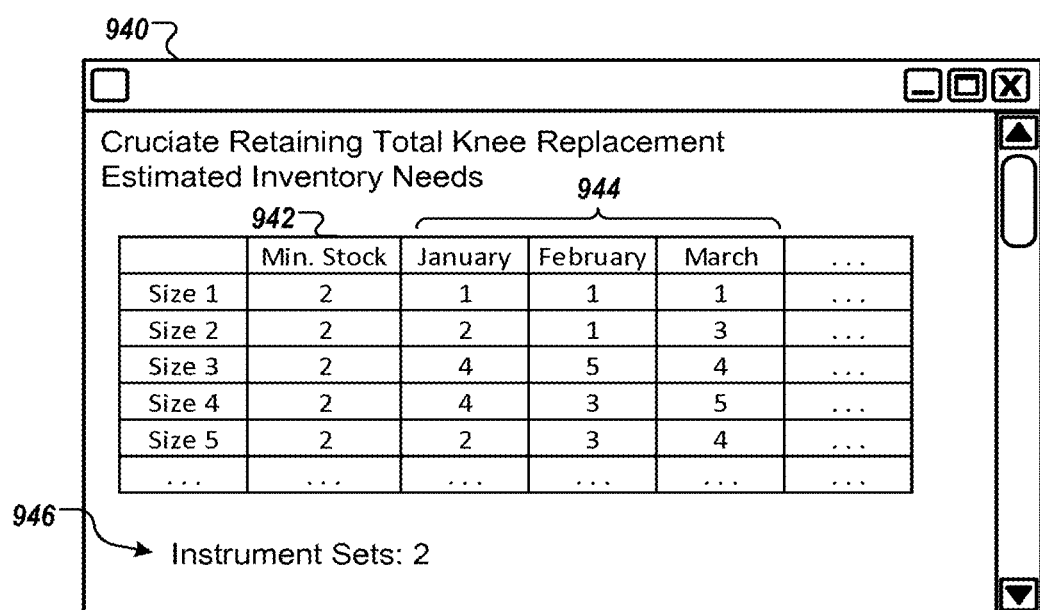
FIG. 9C is a diagram that illustrates an example of a user interface indicating a predicted inventory need.

Referring to FIG. 9C, a user interface 940 provides data indicating the distribution 930, for example, through of the medical facility app 140. The user interface 940 provides minimum inventory levels 942 to meet safety stock requirements. The user interface 940 also indicates expected amounts 944 of implants of various different sizes that will be needed over time, for example, from one month to the next. The user interface 940 also indicates the predicted number of instrument sets 946 needed by the medical facility.

Over time, as inventory at the medical facility is used and replenished, the scheduler 110 may update the predictive model 112 and the distribution 930 that models the needs of the medical facility. For example, as the population of patients changes, or as implants are used at a rate higher than predicted, the distribution 930 may be changed to adjust the supply of implants as needed. To update the distribution 930, the set of estimated or representative patient profiles may be updated to reflect any changes in the patient population. In addition, the predictive model 112 may be adjusted as discussed with respect to FIG. 3B to accurately reflect the probability distribution of items that are used for different patient profiles. The profiles in the updated set of estimated patient profiles may then be input to the adjusted predictive model 112 to generate a new distribution 930 of implants or other items to be stocked at a medical facility.

While various examples discuss knee replacement surgeries, the same techniques may be performed for any other medical procedure. For example, the same techniques may be used for any medical procedure to predict items needed for individual procedures, procure and track items for procedures, monitor patient compliance, and track and predict outcomes. These techniques may be used for arthroplasty procedures, including knee replacements, hip replacements, and shoulder replacements, as well as other orthopaedic procedures. In addition, the same techniques may be used in conjunction with medical procedures involving non-orthopaedic implants and medical procedures that do not involve implants.

A number of implementations have been described. Nevertheless, it will be understood that various modifications may be made without departing from the spirit and scope of the disclosure. For example, various forms of the flows shown above may be used, with steps re-ordered, added, or removed.

In one aspect, the subject matter described in this specification may be embodied in methods for adjusting an inventory of medical supplies at a medical facility that may include the actions of receiving data indicating patient characteristics of a particular patient, inputting the patient characteristics of the particular patient to a predictive model that has been trained using data indicating characteristics of other patients and items used in surgeries for the other patients to predict items likely to be used in surgeries, receiving, from the predictive model in response to inputting the patient characteristics of the particular patient, data indicating items likely to be used in a planned surgery for the particular patient, and adjusting an inventory of medical supplies at a medical facility where the planned surgery for the particular patient is to be performed based on the data indicating items likely to be used in the planned surgery for the particular patient.

Implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

Implementations may each optionally include one or more of the following features. For instance, receiving data indicating items likely to be used in a planned surgery for the particular patient may include receiving, for each of multiple alternative items that may be used in the planned surgery for the particular patient, a probability score that indicates a probability that the item will be used in the planned surgery for the particular patient.

Implementations may include the multiple alternative items including multiple alternative implants for a joint replacement procedure. In such implementations, receiving the probability scores may include receiving a probability score corresponding to each of the alternative implants.

In some implementations, the one or more of the probability scores may indicate a probability that a particular size of implant will be used in the planned surgery for the particular patient.

In some implementations, receiving the data indicating items likely to be used in a planned surgery for the particular patient may include receiving scores that respectively indicate likelihoods that different sizes of implants will be used in the planned surgery for the particular patient.

In some examples, inputting the patient characteristics to the predictive model may include inputting a height of the particular patient, a weight of the particular patient, a sex of the particular patient, an age of the particular patient, a race of the particular patient, or a body mass index of the particular patient.

Implementations may further include inputting, to the predictive model, information identifying a particular surgeon designated to perform the planned surgery for the particular patient, and, in some examples, receiving the data indicating items likely to be used in a planned surgery for the particular patient may include receiving, from the predictive model, data generated based on the patient characteristics for the particular patient and the information identifying the particular surgeon designated to perform the planned surgery for the particular patient.

Implementations may further include inputting, to the predictive model, information identifying preferences of a particular surgeon designated to perform the planned surgery for the particular patient, and in some examples, receiving the data indicating items likely to be used in the planned surgery for the particular patient may include receiving, from the predictive model, data generated based on the patient characteristics for the particular patient and the information identifying the preferences of the particular surgeon designated to perform the planned surgery for the particular patient.

Implementations may further include inputting information identifying a hospital where the planned surgery for the particular patient is to be performed, and in some examples, receiving the data indicating items likely to be used in the planned surgery for the particular patient may include receiving, from the predictive model, data generated based on the patient characteristics for the particular patient and the information indicating the hospital where the planned surgery for the particular patient is to be performed.

Implementations may further include inputting information indicating one or more characteristics of a surgical plan for the planned surgery for the particular patient, and in some examples, receiving the data indicating items likely to be used in the planned surgery for the particular patient may include receiving, from the predictive model, data generated based on the patient characteristics for the particular patient and the information indicating the one or more characteristics of the surgical plan for the planned surgery for the particular patient.

Adjusting the inventory of medical supplies at the medical facility may, for example, include selecting one or more items to be stored at the medical facility based on the data received from the predictive model.

In some examples, selecting the one or more items to be provided may include selecting may include determining, based on the data from the predictive model, that one or more items each have at least a minimum likelihood of being used in the planned surgery for the particular patient, and based on the determination, selecting each of the items that have at least the minimum likelihood.

Selecting the one or more items to be provided may include, in some examples, determining, based on the data from the predictive model, that multiple items that are alternatives for each other have at least a minimum likelihood of being used in the planned surgery for the particular patient, and based on the determination, selecting each of the multiple items that are alternatives for each other that have at least the minimum likelihood to be stored at the medical facility.

In some implementations, the data from the predictive model indicates that a first item is likely to be used in the planned surgery for the particular patient. In some examples, adjusting the inventory of medical supplies at the medical facility may include accessing inventory data indicating contents of the inventory of the medical facility where the planned surgery for the particular patient is to be performed, and based on the accessed inventory data and the data received from the predictive model, determining that the inventory of the medical facility does not include a quantity of the first item likely to be used in a set of planned surgeries including the planned surgery for the particular patient.

In some implementations, adjusting the inventory of medical supplies at the medical facility may include, in response to determining that the inventory of the medical facility does not include the quantity of the first item likely to be used, providing, through an interface with the medical facility, status information indicating that that an additional amount of the first item is likely to be needed at the medical facility.

In some examples, adjusting the inventory of medical supplies at the medical facility may include indicating an action for acquiring the first item, receiving user input authorizing the action, and performing the action in response to receiving the user input.

The action may, for instance, include an action selected from the group consisting of expediting a shipment to the medical facility, the shipment including the first item, initiating a purchase of the first item, requesting the first item from another medical facility, and requesting that a manufacturer of the first item manufacture the first item.

In some examples, performing the action may include accessing data indicating a scheduled date for the planned surgery of the particular patient, determining a shipping mode and shipping date that will provide the first item to the medical facility by the scheduled data of the planned surgery, and instructing a provider of the first item to ship the first item by the shipping date using the shipping mode.

In some implementations, the predictive model may include a set of rules determined using regression analysis, a maximum entropy classifier, an artificial neural network, a support vector machine, or a kernel machine.

In another aspect, the subject matter described in this specification may be embodied in methods of adjusting an inventory of medical supplies at a medical facility that may include the actions of accessing, for each of multiple patients, data indicating a scheduled medical procedure to be performed for the patient at the medical facility and characteristics of the patient, obtaining, for each of the multiple patients, probability data determined based on the patient's characteristics, the probability data indicating likelihoods that items will be used during the medical procedure for the patient, aggregating the probability data for the multiple patients to generate predicted inventory data that indicates predicted quantities of the items needed for the medical procedures of the multiple patients, accessing current inventory data indicating quantities of the items that will be available at the medical facility, determining differences between the predicted inventory data and the current inventory data, and adjusting the amounts of at least some of the items at the medical facility based on the differences between the predicted inventory data and the current inventory data. Other implementations of this and other aspects include corresponding systems, apparatus, and computer programs, configured to perform the actions of the methods, encoded on computer storage devices.

Implementations may each optionally include one or more of the following features. For instance, the current inventory data may indicate items stored at the medical facility and items in transit to the medical facility.

In some implementations, the probability data indicates probabilities that different sizes of implants will be used.

In some implementations, obtaining, for each of the multiple patients, probability data determined based on the patient's characteristics may include obtaining, for each particular patient of the multiple patients, probability data determined based on a height of the particular patient, a weight of the particular patient, a sex of the particular patient, an age of the particular patient, a race of the particular patient, or a body mass index of the particular patient.

In another aspect, the subject matter described in this specification may be embodied in methods for adjusting a predictive model configured to predict medical supplies needed for a medical procedure based on characteristics of the patient receiving the medical procedure that may include the actions of accessing patient data indicating characteristics of a particular patient, accessing prediction data that indicates outputs that a predictive model provided based on receiving the patient data as input, the prediction data indicating probabilities that particular items would be used in a surgical procedure for the particular patient, accessing usage data indicating items that were used in the surgical procedure for the particular patient, adjusting the predictive model based on the prediction data and the usage data, and adjusting an inventory of medical supplies at a medical facility based on output of the adjusted predictive model. Other implementations of this and other aspects include corresponding systems, apparatus, and computer programs, configured to perform the actions of the methods, encoded on computer storage devices.

Implementations may each optionally include one or more of the following features. For instance, adjusting the predictive model based on the prediction data and the usage data may include determining target output values based on the usage data, comparing the outputs of the predictive model with the target output values, and adjusting the predictive model based on differences between the outputs of the predictive model and the target output values.

In some implementations, determining the target output values based on the usage data may include determining a target probability distribution for implant sizes based at least in part on an indication in the usage data of one or more implants that were used in the surgical procedure for the particular patient. Comparing the outputs of the predictive model with the target output values may, for instance, include comparing the target probability distribution with a predicted probability distribution for the implant sizes that is indicated by the prediction data. In addition, adjusting the predictive model based on differences between the outputs of the predictive model and the target output values may include adjusting the predictive model based on differences between the target probability distribution and the predicted probability distribution.

In some implementations, adjusting the predictive model based on the prediction data and the usage data may include adjusting the predictive model to indicate, in response to receiving one or more of the characteristics of the particular patient as input, an increased probability of use for an item that the usage data indicates was used in the surgical procedure for the particular patient.

In some implementations, adjusting the predictive model based on the prediction data and the usage data may include adjusting the predictive model to indicate, in response to receiving one or more of the characteristics of the particular patient as input, a decreased probability of use for an item that the usage data does not indicate was used in the surgical procedure for the particular patient.

In some implementations, the characteristics of the particular patient may include a sex of the particular patient, an age of the particular patient, a weight of the particular patient, a height of the particular patient, a race of the particular patient, or a body mass index of the particular patient.

In some implementations, adjusting the predictive model may include altering parameters of a portion of the predictive model, in some implementations, the portion is (i) a set of rules determined using regression analysis, (ii) a maximum entropy classifier, (iii) an artificial neural network, (iv) a support vector machine, or (v) a kernel machine. The prediction data may, for example, indicate a probability that a particular implant, trial component, surgical tool, or disposable item would be used in the surgical procedure for the particular patient. In addition, the usage data may indicate whether the particular implant, trial component, surgical tool, or disposable item was used in the surgical procedure for the particular patient.

In another aspect, the subject matter described in this specification may be embodied in methods of tracking and analyzing outcomes of medical procedures that may include the actions of storing pre-operative data for multiple patients in one or more databases, the pre-operative data indicating pre-operative regimens for the patients and levels of compliance with the pre-operative regimens by the patients, storing post-operative data for the multiple patients in the one or more databases, the post-operative data indicating post-operative regimens for the patients and levels of compliance with the post-operative regimens by the patients, storing outcome data for the multiple patients in the one or more databases, the outcome data indicating outcomes of medical procedures of the multiple patients, analyzing the data stored in the one or more databases to identify correlations of the pre-operative data and the post-operative data with different outcomes indicated by the outcome data, determining, based on the correlations, measures indicating how compliance or non-compliance with elements of pre-operative or post-operative regimens contribute to the different outcomes indicated by the outcome data, and providing, on a user interface, the measures indicating how compliance or non-compliance with elements of pre-operative or post-operative regimens contribute to the different outcomes. Other implementations of this and other aspects include corresponding systems, apparatus, and computer programs, configured to perform the actions of the methods, encoded on computer storage devices.

Implementations may each optionally include one or more of the following features. For instance, providing the measures may include providing indications of likely causes of the different outcomes indicated by the outcome data.

Implementations may further include storing procedure data for the multiple patients in the one or more databases, the procedure data indicating characteristics of the medical procedures for the multiple patients. In some implementations, analyzing the data may include analyzing the data stored in the one or more databases to identify correlations of the pre-operative data, the procedure data, and the post-operative data with the different outcomes indicated by the outcome data.

In some implementations, the procedure data indicates surgical events that occurred during the medical procedures of the multiple patients or surgical techniques used during the medical procedures of the multiple patients. Implementations may further include determining measures indicating how the surgical events or surgical techniques are likely to affect outcomes of the medical procedures.

Implementations may include storing patient data for the multiple patients in the one or more databases where the patient data for each patient includes patient characteristics including a sex of the patient, an age of the patient, a weight of the patient, a height of the patient, a race of the patient, or a body mass index of the patient. In some implementations, analyzing the data may include analyzing the data stored in the one or more databases to identify correlations of the pre-operative data, the patient data, and the post-operative data with the different outcomes indicated by the outcome data. Implementations may further include determining measures indicating how one or more of the patient characteristics are likely to affect outcomes of the medical procedures.

Implementations may further include receiving data indicating characteristics of a particular patient, based on the characteristics of the particular patient and the correlations of the patient data and the outcome data, determining a classification for the particular patient or predicting a likely outcome of a procedure for the patient.

In some implementations, analyzing the data stored in the one or more databases may include identifying a subset of the multiple patients that the outcome data indicates have experienced above-average outcomes, analyzing the pre-operative data, the post-operative data, and the outcome data for the patients in the subset to identify factors correlated with the above-average outcomes.

In some implementations, the outcome data indicates re-admission events or patient satisfaction levels for the multiple patients. Determining the measures may, for instance, include determining that one or more pre-operative or post-operative patient actions contribute to reduced re-admission rates or increased patient satisfaction rates.

Implementations may further include determining, based on the pre-operative data, the post-operative data, and the outcome data, that an action has less than a threshold level of correlation with an outcome of a medical procedure, altering a pre-operative regimen, post-operative regimen, or surgical plan for the medical procedure to omit the action that has less than the threshold level of correlation with the outcome of the medical procedure.

In some implementations, the pre-operative data and the post-operative data indicate compliance with prescribed patient actions that include medication intake, physical therapy participation, or physical activity of a patient. In addition, determining the measures may include determining measures indicating an extent that medication intake, physical therapy participation, or physical activity of a patient contribute to the different outcomes.

In another aspect, the subject matter described in this specification may be embodied in methods of adjusting production or distribution of medical supplies that may include the actions of accessing, for each of multiple patients, data indicating a scheduled medical procedure to be performed for the patient and characteristics of the patient, obtaining, for each of the multiple patients, probability data determined based on the patient's characteristics, the probability data indicating likelihoods that items will be used during the medical procedure for the patient, aggregating the probability data for the multiple patients to generate predicted inventory data that indicates predicted quantities of the items needed for the medical procedures of the multiple patients, and adjusting quantities of items that are manufactured or distributed based on the predicted inventory data. Other implementations of this and other aspects include corresponding systems, apparatus, and computer programs, configured to perform the actions of the methods, encoded on computer storage devices.

Implementations may each optionally include one or more of the following features. For instance, adjusting the quantities of the items that are produced or distributed based on the predicted inventory data may include determining quantities of implants to manufacture for each of a plurality of implant sizes based on the predicted inventory data, and manufacturing the determined quantities of implants for the plurality of implant sizes.

In some implementations, aggregating the probability data for the multiple patients to generate predicted inventory data may include aggregating probability data for patients associated with a particular medical facility, a particular distribution center, or a particular geographical region. In these implementations, adjusting the quantities of the items that are produced or distributed based on the predicted inventory data may include determining, based on the predicted inventory data, quantities of implants to ship to the particular medical facility, the particular distribution center, or the particular geographical region where the determined quantities respectively correspond to different implant sizes, and shipping, to the particular medical facility, the particular distribution center, or the particular geographical region, implants in the different implant sizes according to the quantities respectively corresponding to the different implant sizes.

In some implementations, adjusting the quantities of the items that are produced or distributed based on the predicted inventory data may include determining, based on a first manufacturing or distribution plan, a planned quantity of an implant of a particular size that are planned to be manufactured or distributed, determining, based on the predicted inventory data, a predicted quantity of implants of the particular size that are predicted for the medical procedures of the multiple patients, comparing the planned quantity with the predicted quantity, and altering the first manufacturing or distribution plan based on comparing the planned quantity with the predicted quantity.

In some implementations, adjusting the quantities of the items that are produced or distributed based on the predicted inventory data may include determining that a planned quantity of implants of a particular size that is planned to be manufactured during a time period is greater than a predicted quantity of implants of the particular size indicated by the predicted inventory data, and based on determining that the planned quantity is greater than the predicted quantity, manufacturing fewer than the planned quantity of implants of the particular size during the time period.

In some implementations, adjusting the quantities of the items that are produced or distributed based on the predicted inventory data may include determining that a planned quantity of implants of a particular size that is planned to be manufactured during a time period is greater than a predicted quantity of implants of the particular size indicated by the predicted inventory data, and based on determining that the planned quantity is less than the predicted quantity, manufacturing more than the planned quantity of implants of the particular size during the time period.

In some implementations, adjusting the quantities of the items that are produced or distributed based on the predicted inventory data may include determining that a planned quantity of implants of a particular size that is planned to be delivered to a destination during a time period is greater than a predicted quantity of implants of the particular size indicated by the predicted inventory data, and based on determining that the planned quantity is greater than the predicted quantity, delivering fewer than the planned quantity of implants of the particular size to the destination during the time period.

In some implementations, adjusting the quantities of the items that are produced or distributed based on the predicted inventory data may include determining that a planned quantity of implants of a particular size that is planned to be delivered to a destination during a time period is less than a predicted quantity of implants of the particular size indicated by the predicted inventory data, and based on determining that the planned quantity is greater than the predicted quantity, delivering more than the planned quantity of implants of the particular size to the destination during the time period.

In some implementations, obtaining, for each of the multiple patients, probability data determined based on the patient's characteristics may, for example, include obtaining, for each particular patient of the multiple patients, probability data determined based on a height of the particular patient, a weight of the particular patient, a sex of the particular patient, an age of the particular patient, a race of the particular patient, or a body mass index of the particular patient.

In another aspect, the subject matter described in this specification may be embodied in methods of managing inventory of a medical facility that may include the actions of receiving data indicating use of an item in a medical procedure, in response to receiving data indicating the use of the item, determining that the item should be replaced in the inventory of the medical facility. Based on determining that the item should be replaced, these methods may further include the actions of identifying a price for the item indicated by a contract with a supplier, and transmitting, to the supplier, an order to purchase the item from the supplier at the price indicated by the contract with the supplier.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

Implementations may each optionally include one or more of the following features. For instance, receiving the data indicating use of an item in a medical procedure may include receiving data indicating a scan of a tracking device associated with the item, the scan identifying the item.

In some implementations, the tracking device may include an optical code or radio-frequency identification device. In some implementations, receiving data indicating a scan of the tracking device may include, receiving, during the medical procedure, scan data generated by a scan of the tracking device occurring during the medical procedure, the tracking device being scanned in the operating room where the medical procedure is performed.

In some implementations, receiving the data indicating use of an item in a medical procedure may include receiving data entered by medical personnel from electronic medical records for the medical procedure.

In some implementations, determining that the item should be replaced in the inventory of the medical facility may include determining that a quantity of the item in inventory at the medical facility is less than a minimum quantity for the item.

In some implementations, determining that the item should be replaced in the inventory of the medical facility may include, for example, accessing prediction data indicating likelihoods that different items will be used in a set of multiple medical procedures scheduled to occur at the medical facility during a time period, and determining, based on the prediction data, that a quantity of the item in inventory at the medical facility is less than a predicted quantity of the item that is likely to be used during the time period for the set of multiple medical procedures scheduled to occur at the medical facility during the time period. In some implementations, transmitting the order to purchase the item may include transmitting the order to purchase the item directly to a manufacturer of the item.

Implementations may further include generating the order to purchase the item from the supplier, providing data about the order to a user, and receiving authorization to submit the order from the user. In some implementations, transmitting the order to purchase the item may be performed in response to receiving authorization to submit the order from the user.

In some implementations, determining that the item should be replaced, identifying the price for the item, and transmitting the order to purchase the item are each performed automatically by the one or more computers without requiring input from a human user.

In some implementations, determining that the item should be replaced, identifying the price for the item, and transmitting the order to purchase the item are each performed before the medical procedure is completed.

In some implementations, determining that the item should be replaced, identifying the price for the item, and transmitting the order to purchase the item are each performed the same day the medical procedure is performed.

In some implementations, identifying a price for the item indicated by a contract with a supplier may include accessing contract data indicating terms of contracts between the medical facility and a plurality of suppliers, identifying, based on the contract data, multiple prices for the item indicated by different contracts with one or more suppliers offering the item for sale, and identifying, from among the multiple prices, the lowest price for the item and a particular supplier that has contractually agreed to sell the item at the lowest price.

All of the functional operations described in this specification may be implemented in digital electronic circuitry, or in computer software, firmware, or hardware, including the structures disclosed in this specification and their structural equivalents, or in combinations of one or more of them. The techniques disclosed may be implemented as one or more computer program products, i.e., one or more modules of computer program instructions encoded on a computer-readable medium for execution by, or to control the operation of, data processing apparatus. The computer readable-medium may be a machine-readable storage device, a machine-readable storage substrate, a memory device, a composition of matter affecting a machine-readable propagated signal, or a combination of one or more of them. The computer-readable medium may be a non-transitory computer-readable medium. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in, special purpose logic circuitry.

To provide for interaction with a user, the techniques disclosed may be implemented on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input.

Implementations may include a computing system that includes a back end component, e.g., as a data server, or that includes a middleware component, e.g., an application server, or that includes a front end component, e.g., a client computer having a graphical user interface or a Web browser through which a user may interact with an implementation of the techniques disclosed, or any combination of one or more such back end, middleware, or front end components. The components of the system may be interconnected by any form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

Thus, particular implementations have been described. Other implementations are within the scope of the following claims. For example, the actions recited in the claims may be performed in a different order and still achieve desirable results.

What is claimed is:

1. A method of reducing hospital readmissions, the method comprising:
   receiving pre-operative data for a plurality of first patients, wherein the pre-operative data for each first patient comprises a pre-operative regimen for the first patient and a compliance level with the pre-operative regimen for the first patient, wherein each first patient underwent a medical procedure;
   receiving post-operative data for the plurality of first patients, wherein the post-operative data for each first patient comprises a post-operative regimen for the first patient and a compliance level with the post-operative regimen for the first patient;
   receiving outcome data for the plurality of first patients, wherein the outcome data for each first patient comprises an outcome of the medical procedure for the first patient;
   receiving surgeon data for each surgeon that performed each medical procedure, the surgeon data comprising a surgical technique used to perform the medical procedure for each first patient;
   developing a predictive model based on the pre-operative data, the post-operative data, the surgeon data, and the outcome data, the predictive model configured to identify correlations between the pre-operative data and the post-operative data and the outcomes indicated by the outcome data;
   receiving, by the predictive model, patient data associated with a second patient scheduled to undergo the medical procedure;
   calculating, by the predictive model, a predicted readmission rate associated with the medical procedure for the second patient based on the patient data;
   generating, based on the predicted readmission rate and the identified correlations between the pre-operative data and the post-operative data and the outcomes indicated by the outcome data, a pre-operative plan and a post-operative plan for the second patient scheduled to undergo the medical procedure; and
   providing a surgical technique for the medical procedure for the second patient based on the predicted readmission rate and the identified correlations between the pre-operative data and the post-operative data and the outcomes indicated by the outcome data.

2. The method of claim 1, wherein receiving pre-operative data comprises receiving a response to each of one or more questions posed to the first patient.

3. The method of claim 1, wherein receiving pre-operative data comprises receiving sensor information from one or more sensors located in proximity to the first patient.

4. The method of claim 1, wherein receiving pre-operative data comprises receiving information from a medical professional.

5. The method of claim 1, wherein receiving pre-operative data comprises receiving an electronic medical record pertaining to the first patient.

6. The method of claim 1, wherein receiving post-operative data comprises receiving a response to each of one or more questions posed to the first patient.

7. The method of claim 1, wherein receiving post-operative data comprises receiving sensor information from one or more sensors located in proximity to the first patient.

8. The method of claim 1, wherein receiving post-operative data comprises receiving information from a medical professional.

9. The method of claim 1, wherein receiving post-operative data comprises receiving an electronic medical record pertaining to the first patient.

10. The method of claim 1, wherein the medical procedure comprises one of a joint implant procedure and a joint implant revision procedure.

11. A system comprising:
    a processor unit, configured to:
       receive pre-operative data for a plurality of first patients, wherein the pre-operative data for each first patient comprises a pre-operative regimen for the first patient and a compliance level with the pre-operative regimen for the first patient, wherein each first patient underwent a medical procedure,
       receive post-operative data for the plurality of first patients, wherein the post-operative data for each first patient comprises a post-operative regimen for the first patient and a compliance level with the post-operative regimen for the first patient,
       receive outcome data for the plurality of first patients, wherein the outcome data for each first patient comprises an outcome of the medical procedure for the first patient,
       receive surgeon data for each surgeon that performed each medical procedure, the surgeon data comprising a surgical technique used to perform the medical procedure for each first patient,
       develop a predictive model based on the pre-operative data, the post-operative data, the surgeon data, and the outcome data, the predictive model configured to identify correlations between the pre-operative data and the post-operative data and the outcomes indicated by the outcome data,
       receive, by the predictive model, patient data associated with a second patient scheduled to undergo the medical procedure,
       calculate, by the predictive model, a predicted readmission rate associated with the medical procedure for the second patient based on the patient data, generate, based on the predicted readmission rate and the identified correlations between the pre-operative data and the post-operative data and the outcomes indicated by the outcome data, a pre-operative plan and a post-operative plan for the second patient scheduled to undergo the medical procedure, and provide a surgical technique for the medical procedure for the second patient based on the predicted readmission rate and the identified correlations between the pre-operative data and the post-operative data and the outcomes indicated by the outcome data; and a graphical user interface unit coupled to the processor unit, the graphical user interface unit configured to:

receive a type of medical procedure, and display the pre-operative plan and the post-operative plan.

12. A non-transitory machine-readable storage medium including instructions that, when executed by a machine, cause the machine to:

receive pre-operative data for a plurality of first patients, wherein the pre-operative data for each first patient comprises a pre-operative regimen for the first patient and a compliance level with the pre-operative regimen for the first patient, wherein each first patient underwent a medical procedure;

receive post-operative data for the plurality of first patients, wherein the post-operative data for each first patient comprises a post-operative regimen for the first patient and a compliance level with the post-operative regimen for the first patient;

receive outcome data for the plurality of first patients, wherein the outcome data for each first patient comprises an outcome of the medical procedure for the first patient;

receive surgeon data for each surgeon that performed each medical procedure, the surgeon data comprising a surgical technique used to perform the medical procedure for each first patient;

develop a predictive model based on the pre-operative data, the post-operative data, the surgeon data, and the outcome data, the predictive model configured to identify correlations between the pre-operative data and the post-operative data and the outcomes indicated by the outcome data;

receive, by the predictive model, patient data associated with a second patient scheduled to undergo the medical procedure;

calculate, by the predictive model, a predicted readmission rate associated with the medical procedure for the second patient based on the patient data;

generate, based on the predicted readmission rate and the identified correlations between the pre-operative data and the post-operative data and the outcomes indicated by the outcome data, a pre-operative plan and a post-operative plan for the second patient scheduled to undergo the medical procedure; and provide a surgical technique for the medical procedure for the second patient based on the predicted readmission rate and the identified correlations between the pre-operative data and the post-operative data and the outcomes indicated by the outcome data.

* * * * *